US011937808B2

(12) United States Patent
Campbell et al.

(10) Patent No.: US 11,937,808 B2
(45) Date of Patent: Mar. 26, 2024

(54) SMALL BONE FIXATION SYSTEMS AND METHODS

(71) Applicant: CrossRoads Extremity Systems, LLC, Memphis, TN (US)

(72) Inventors: Michael Campbell, Virginia Beach, VA (US); Daniel Sayger, Olive Branch, MS (US); Michael Chad Hollis, Collierville, TN (US)

(73) Assignee: CrossRoads Extremity Systems, LLC, Memphis, TN (US)

( * ) Notice: Subject to any disclaimer, the term of this patent is extended or adjusted under 35 U.S.C. 154(b) by 88 days.

(21) Appl. No.: 17/194,894

(22) Filed: Mar. 8, 2021

(65) Prior Publication Data
US 2021/0298748 A1 Sep. 30, 2021

Related U.S. Application Data

(60) Provisional application No. 62/987,299, filed on Mar. 9, 2020.

(51) Int. Cl.
| | | |
|---|---|---|
| *A61B 17/064* | (2006.01) | |
| *A61B 17/00* | (2006.01) | |
| *A61B 17/10* | (2006.01) | |
| *A61B 17/17* | (2006.01) | |
| *A61B 17/56* | (2006.01) | |
| *A61B 17/68* | (2006.01) | |

(Continued)

(52) U.S. Cl.
CPC .......... *A61B 17/0642* (2013.01); *A61B 17/17* (2013.01); *A61B 17/864* (2013.01); *A61B 2017/00668* (2013.01); *A61B 17/0644* (2013.01); *A61B 2017/0645* (2013.01); *A61B 17/10* (2013.01); *A61B 17/1714* (2013.01); *A61B 2017/564* (2013.01); *A61B 2017/681* (2013.01); *A61F 2/0811* (2013.01); *A61F 2002/0858* (2013.01)

(58) Field of Classification Search
CPC ............ A61B 17/0644; A61B 17/8875; A61B 17/068; A61B 17/1728; A61B 17/1714; A61B 17/17; A61B 17/10; A61B 17/0642; A61B 2017/00668; A61B 2017/681; A61B 2017/0645; A61F 2/0811; A61F 2002/0858; Y10S 411/92
USPC .......................................................... 606/75
See application file for complete search history.

(56) References Cited

U.S. PATENT DOCUMENTS

| | | | | |
|---|---|---|---|---|
| 5,662,655 A | * | 9/1997 | Laboureau | A61B 17/0642 606/301 |
| 2007/0123876 A1 | | 5/2007 | Czartoski et al. | |

(Continued)

FOREIGN PATENT DOCUMENTS

WO 2008/149308 A1 12/2008

*Primary Examiner* — Marcela I. Shirsat
(74) *Attorney, Agent, or Firm* — BakerHostetler

(57) ABSTRACT

A bone fixation system can be used to stabilize two bone portions intended to be fused together. The system include a bone staple or clip that includes a cross bar and two legs. The system can include a plurality of screws or other additional implant(s) configured to be implanted at an angle to the legs of the bone staple on opposite sides of the interface between two bone portions. The system can improve fixation strength and/or stability of the two bone portions. The fixation system can be used, for example, in small bones such as bones in the foot or hand.

20 Claims, 36 Drawing Sheets

(51) Int. Cl.
*A61B 17/86* (2006.01)
*A61F 2/08* (2006.01)

(56) References Cited

U.S. PATENT DOCUMENTS

| | | | | |
|---|---|---|---|---|
| 2009/0287249 | A1* | 11/2009 | Reynolds | A61B 17/8052 |
| | | | | 606/301 |
| 2012/0228355 | A1* | 9/2012 | Combrowski | A61B 17/0642 |
| | | | | 227/175.1 |
| 2017/0181779 | A1* | 6/2017 | Leither | A61B 17/809 |
| 2018/0317906 | A1 | 11/2018 | Hollis et al. | |
| 2020/0038076 | A1* | 2/2020 | Amis | A61B 17/808 |

* cited by examiner

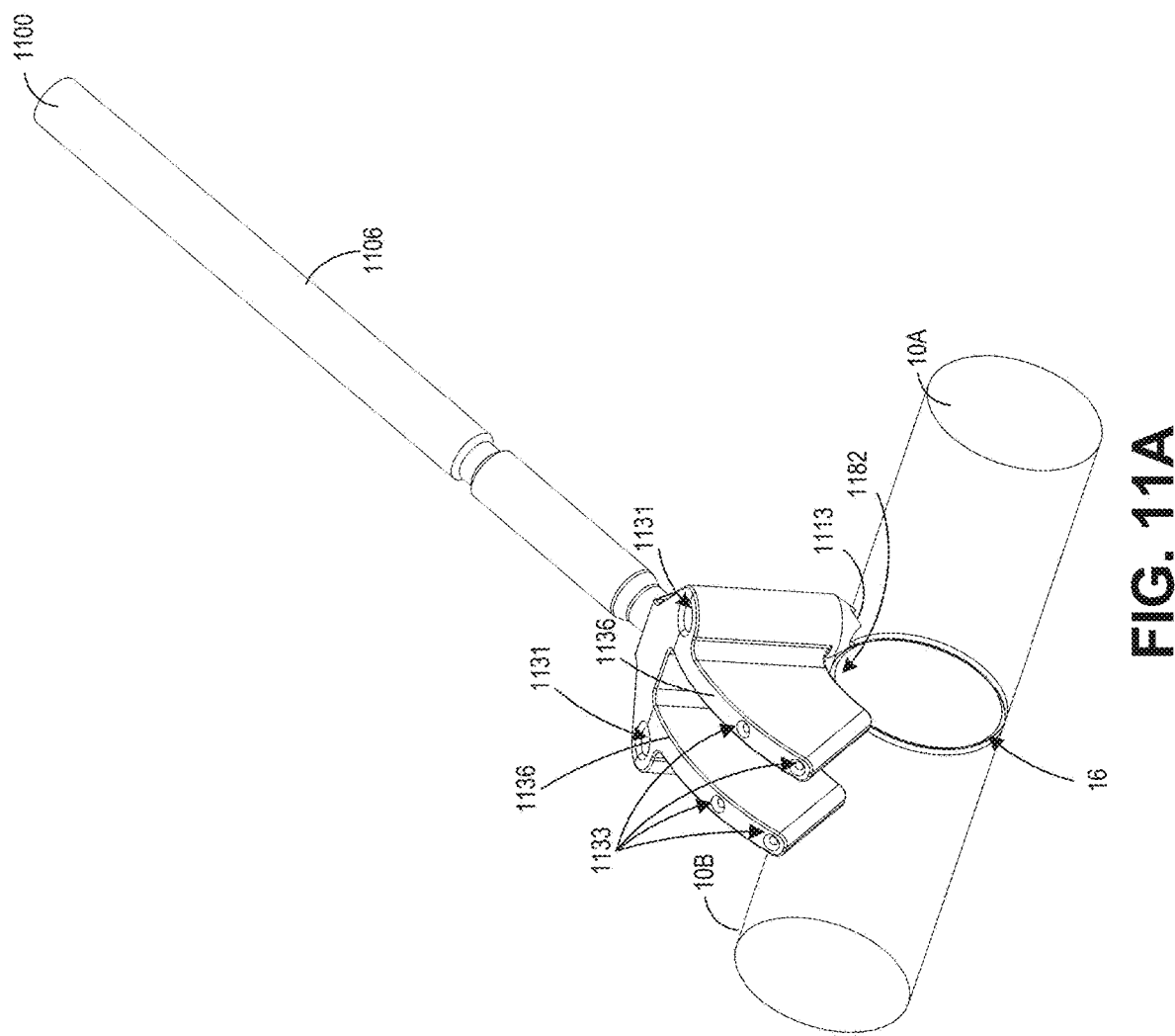

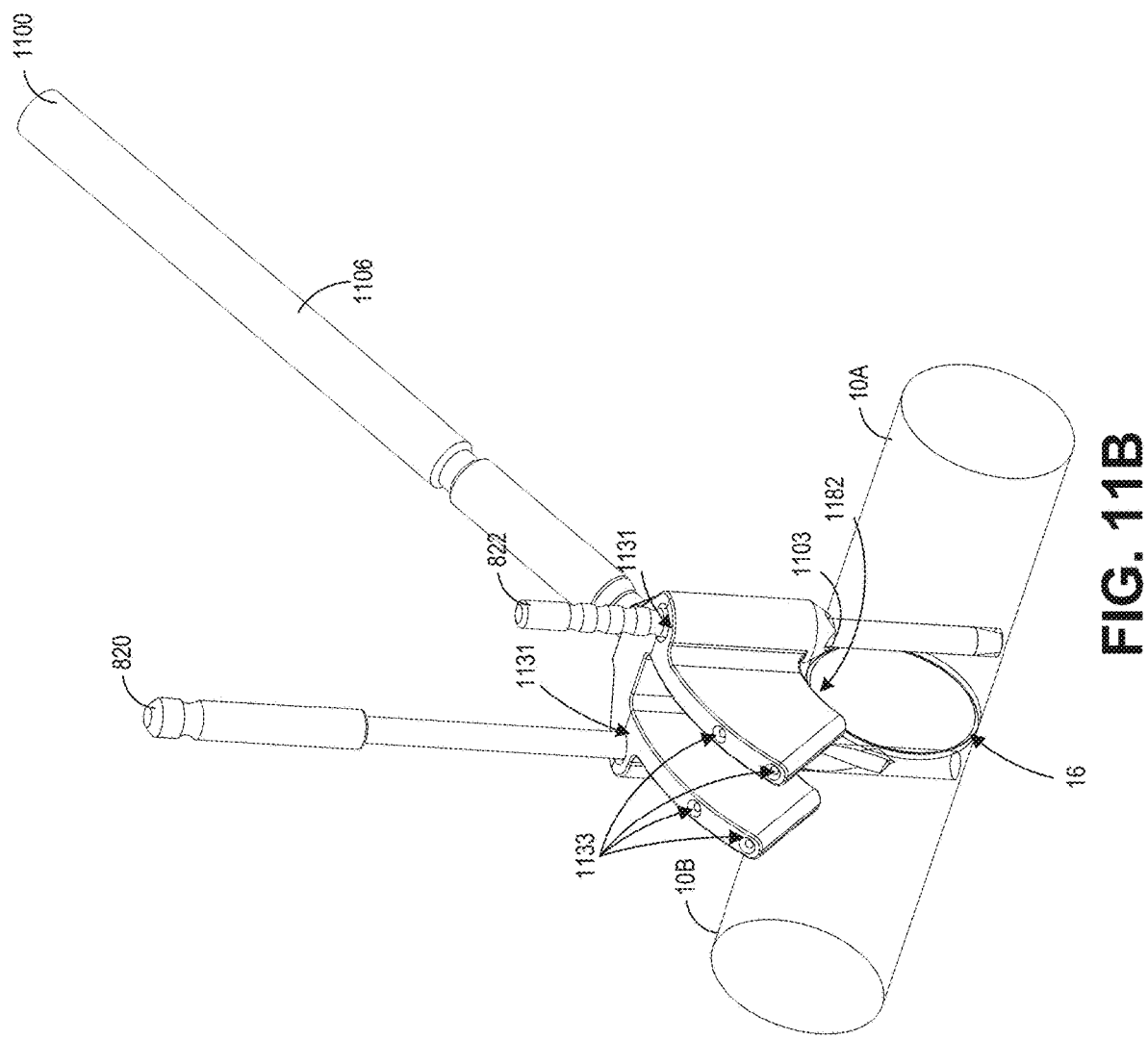

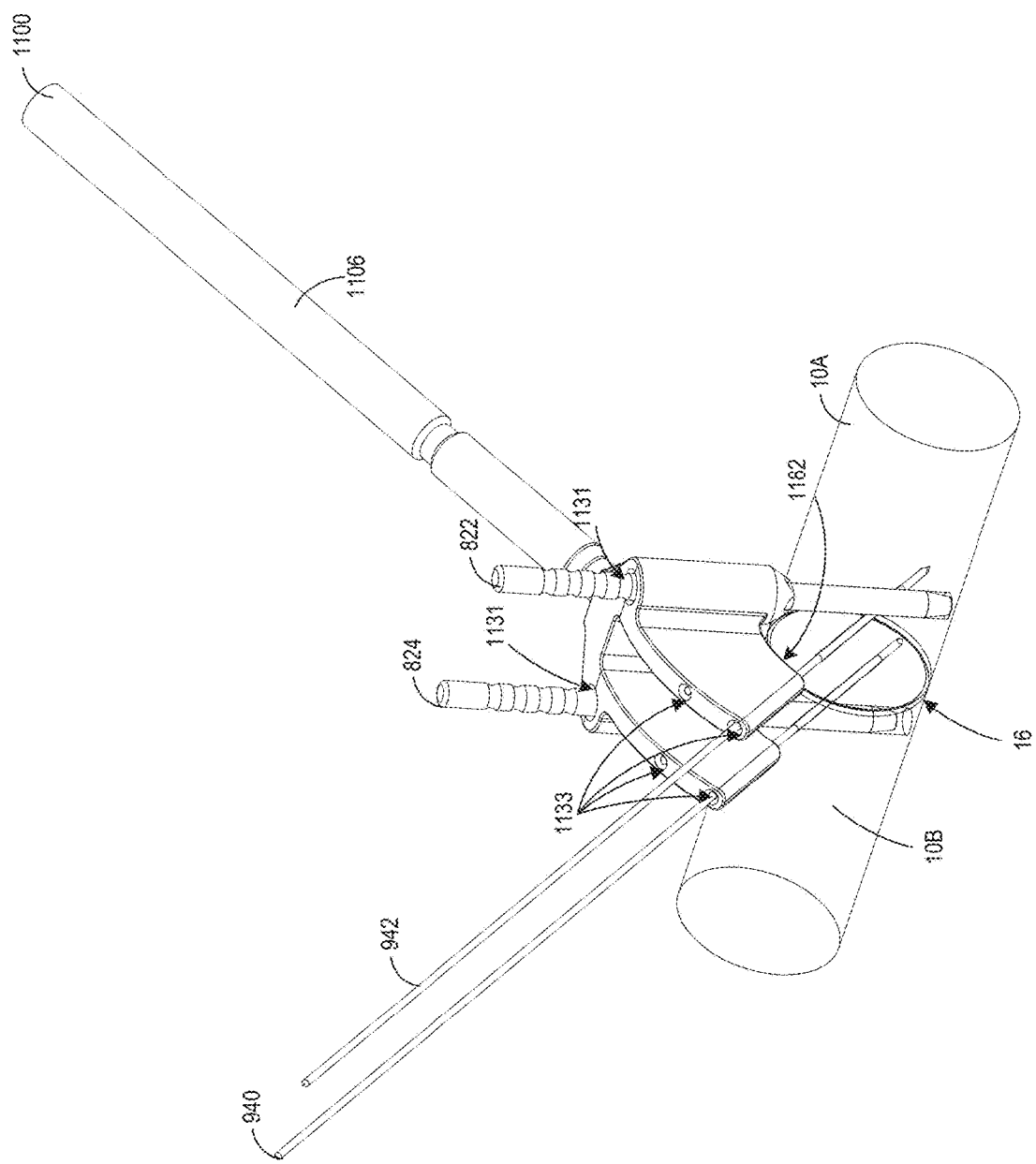

SMALL BONE FIXATION SYSTEMS AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the priority benefit of U.S. Provisional Application No. 62/987,299, filed Mar. 9, 2020, the entirety of which is incorporated herein by reference.

FIELD

The present disclosure relates to small bone fixation systems. More specifically, the present disclosure relates to implants, instrumentation, and methods for small bone fracture fixation.

BACKGROUND

There are many circumstances in which bones or bone fragments need to be fused together, united, or otherwise permanently joined. Some non-limiting examples include arthrodesis, corrective osteotomy, and/or fracture. Micro motions at a discontinuity between two bones or bone fragments can slow down healing or fusion of the bones or bone fragments. The bones or bone fragments heal better and/or faster when they are stabilized with some mechanical load or stress across the discontinuity, for example when the bones or bone fragments are compressed together. The compressive force can reduce micro motions at the discontinuity in bones or bone fragments.

SUMMARY

The various systems and methods of the present disclosure have been developed in response to the present state of the art, and in particular, in response to the problems and needs in the art that have not yet been fully solved by currently available techniques. The systems and methods of the present disclosure can provide techniques for small bone fixation which result in a more stable fixation, faster recovery, and/or improved patient outcomes.

In the present disclosure, an example bone fixation system configured to be implanted across a discontinuity in a bone or across a joint between two bones can comprise at least one elongate implant; and a clip including a first leg and a second leg, the clip further including a bridge connecting the first and second legs at first ends of the first and second legs respectively, wherein a distance between second, free ends of the first and second legs opposite the first ends is configured to increase when the clip changes from a first configuration to a second, deformed configuration, wherein, when moving to the second, deformed configuration, the bridge is elastically deformed such that free ends of the first and second legs move away from each other, and wherein the at least one elongate implant and the first leg of the clip are configured to be implanted on a first side of the discontinuity or joint, the at least one elongate implant being at an angle with the first leg of the clip.

In a configuration, the at least one elongate implant can comprise a first elongate implant; a second elongate implant; and wherein the first elongate implant and the first leg of the clip can be configured to be implanted on the first side of the discontinuity or joint and the second elongate implant and the second leg of the clip are configured to be implanted on a second side of the discontinuity or joint, the first elongate implant being at a first angle with the first leg of the clip, the second elongate implant being at a second angle with the second leg of the clip.

In a configuration, the first and second legs of the clip can have a length such that the second, free ends of the first and second legs terminate in a cancellous portion of the bone or bone portions when implanted.

In a configuration, the at least one elongate implant can comprise a first screw and a second screw.

In a configuration, the first screw and the second screw can have a length such that the first and second screws are configured to achieve bicortical purchase when implanted.

In a configuration, leading ends of the first and second screws can be configured to protrude from an outer surface of the bone or bone portions when implanted.

In a configuration, the first and/or second screws can be cannulated.

In a configuration, the first and/or second screws can be non-cannulated.

In a configuration, the system can comprise a fixation plate configured to be coupled to the first and second screws when implanted.

In a configuration, the at least one elongate implant can comprise first and second legs of a second clip, the second clip further including a bridge connecting the first and second legs of the second clip at first ends of the first and second legs of the second clip respectively, wherein a distance between second, free ends of the first and second legs of the second clip opposite the first ends of the first and second legs of the second clip can be configured to increase when the second clip changes from a free configuration to a deformed configuration.

In a configuration, the first and second legs of the second clip can have a length such that the second, free ends of the first and second legs of the second clip terminate in a cancellous portion of the bone or bone portions when implanted.

In a configuration, the first angle can be the same as the second angle.

In the present disclosure, an example bone fixation system configured to be implanted across a discontinuity in a bone or across a joint between two bones can comprise at least one elongate implant; and a clip including a first leg and a second leg, the clip further including a bridge connecting the first and second legs at first ends of the first and second legs respectively, wherein a distance between second, free ends of the first and second legs opposite the first ends can be configured to increase when the clip changes from a first configuration to a second, deformed configuration, wherein, when moving to the second, deformed configuration, the bridge can be elastically deformed such that free ends of the first and second legs move away from each other, and wherein the at least one elongate implant and the first leg of the clip can be configured to be implanted on a first side of the discontinuity or joint and the second leg of the clip are configured to be implanted on a second side of the discontinuity or joint.

In a configuration, the first and second legs of the clip can have a length such that the second, free ends of the first and second legs terminate in a cancellous portion of the bone or bone portions when implanted.

In a configuration, the at least one elongate implant can comprise a screw.

In a configuration, the screw has a length that can be configured to achieve bicortical purchase when implanted.

In a configuration, the leading end of the at least one screw can be configured to protrude from an outer surface of the bone or bone portions when implanted.

In a configuration, the at least one second screw can be cannulated.

In a configuration, the at least one screw can be non-cannulated.

In a configuration, the system can comprise a fixation plate configured to be coupled to the at least one screw when implanted.

In the present disclosure, an example drill guide configured to deliver any configuration of the above-described system can comprise a fist pair of locating holes configured to guide a drill bit to drill holes on opposite sides of the discontinuity or joint for receiving the first and second legs of the clip; at least one second pair of locating holes configured to guide the drill bit or a different drill bit or bone punch to form holes on opposite sides of the discontinuity for receiving the first and second elongate implants, or to guide insertion of k-wires on opposite sides of the discontinuity for receiving the first and second elongate implants.

In a configuration, a fist pair of locating holes and the at least one second pair of locating holes can be located on a single component.

In a configuration, the at least one second pair of locating holes can be offset from the first pair of locating holes by a distance.

In a configuration, the at least one second pair of locating holes can be separated by a shorter distance than the first pair of locating holes.

In a configuration, the at least one second pair of locating holes can be sized for receiving a k-wire.

In a configuration, the at least one second pair of locating holes can be sized for drilling holes configured to receive a non-cannulated screw.

In a configuration, the at least one second pair of locating holes can be sized to receive a guide tube, and the guide tube can be configured to slidably receive a k-wire.

In a configuration, the first pair of locating holes can be configured to guide the drill bit to drill holes without crossing the discontinuity.

In a configuration, the at least one second pair of locating holes can be configured to guide the drill bit or the other different drill bit or bone punch to form holes, or to guide insertion of the k-wires without crossing the discontinuity.

In a configuration, the at least one second pair of locating holes can comprise two or more pair of locating holes that are at different angles to the first pair of locating holes.

In a configuration, the drill guide can comprise a pair of temporary fixation pins configured to be inserted through the first pair of locating holes and the drilled holes on the bone or bone portions for receiving the first and second legs of the clip prior to forming the holes for receiving the first and second elongate implants or prior to inserting k-wires.

In a configuration, a kit can comprise any configuration of the bone fixation system described above and any configuration of the drill guide described above.

In the present disclosure, an example surgical guide system configured to aid in delivering any configuration of the above-described system can comprise a clip drill guide configured to be positioned across the discontinuity or joint, the clip drill guide comprising a first cannula configured to be positioned on the first side of the discontinuity or joint and a second cannula configured to be positioned on the second side of the discontinuity or joint; and an implant guide configured to be positioned on the first or second side of the discontinuity or joint, the implant guide comprising a plurality of implant positioning holes running through the implant guide and a plurality of guide positioning holes running through the implant guide, the plurality of implant positioning holes being separated from the plurality of guide positioning holes by a distance.

In a configuration, the first and second cannulas are configured to guide drilling of the first and second clip leg holes without crossing the discontinuity or joint.

In a configuration, comprising a first temporary pin configured to be inserted through the first cannula and into a first clip leg hole in the bone or bone portions drilled through the first cannula, and a second temporary pin configured to be inserted through the second cannula and into a second clip leg hole in the bone or bone portions drilled through the second cannula.

In a configuration, the plurality of guide positioning holes running through the implant guide are configured to slidably receive the first and/or second temporary pins.

In a configuration, the plurality of implant positioning holes are configured to receive a hole creation device configured to form a first implant hole or a second implant hole in the bone or bone portions.

In a configuration, the first and/or second implant holes are configured to each receive a non-cannulated screw.

In a configuration, the hole creation device comprises a drill bit or a bone punch.

In a configuration, the plurality of implant positioning holes are configured to receive a k-wire.

In a configuration, the plurality of implant positioning holes are configured to guide the hole creation device or the k-wire through the bone or bone portions without crossing the discontinuity or joint.

In a configuration, the plurality of implant positioning holes are positioned closer to the discontinuity or joint than the plurality of guide positioning holes.

In a configuration, the implant guide is arc-shaped, the plurality of implant positioning holes passing through the implant guide at varying angles and the plurality of guide positioning holes passing through the implant guide at varying angles.

In a configuration, a kit can comprise any configuration of the bone fixation system described above and any configuration of the surgical guide system described above.

In the present disclosure, an example method of fixing bone portions defined by a discontinuity in a bone or fixing two bones across a joint can comprise delivering a first elongate implant into a bone or bone portion on a first side of the discontinuity or joint; delivering a second elongate implant into a bone or bone portion on a second side of the discontinuity or joint; and delivering a clip into the bones or bone portions, a first leg of the clip on the first side of the discontinuity or joint, a second leg of the clip on the second side of the discontinuity or joint, and a bridge connecting first ends of the first and second legs extending across the discontinuity or joint, wherein the clip can be biased to be in a first configuration and wherein the clip can be delivered in a second deformed configuration such that a distance between free ends of the first and second legs of the clip is increased relative to the first configuration, wherein the first elongate implant can be positioned between the first leg of the clip and the discontinuity or joint and the second elongate implant is positioned between the second leg of the clip and the discontinuity or joint, and wherein the first elongate implant can be at a first angle with the first leg of the clip and the second elongate implant is at a second angle with the second leg of the clip.

In a configuration, the method can further comprise pre-drilling holes in the bone or bone portions, the holes configured to receive the first elongate implant, the second elongate implant, and/or the first and second legs of the clip.

In a configuration, the pre-drilling can comprise using a clip drill guide to locate the holes for the first and second legs of the clip.

In a configuration, the pre-drilling can comprise using an implant guide to locate the holes for the first and second elongate implants.

In a configuration, the clip drill guide and the implant guide can comprise an integral device.

In a configuration, the implant guide can comprise a plurality of holes for selection of the first and/or second angles.

In a configuration, the plurality of holes can comprise holes sized for delivery of a non-cannulated screw.

In a configuration, the first and/or second elongate implants can comprise non-cannulated screw(s).

In a configuration, the plurality of holes can comprise holes sized for a k-wire configured to deliver of a cannulated screw.

In a configuration, the first and/or second elongate implants can comprise cannulated screw(s).

In a configuration, the holes for the first and second elongate implants can be offset from the holes to locate the first and second legs by a distance.

In a configuration, the first and second angles can be substantially the same such that the first and second elongate implants are generally parallel to each other.

In a configuration, the first and second angles can be different such that the first and second elongate implants are at an angle with each other.

In a configuration, the first and second elongate implants each can have a length greater than a length of the first or second legs such that the first and second elongate implants are each configured to achieve bicortical purchase.

In a configuration, the first and/or second elongate implants can be delivered so that leading ends of the first and/or second elongate implants protrude from an outer surface of the bone or bone portions.

In a configuration, delivering the first elongate implant and delivering the second elongate implant can comprise delivering first and second legs of a second clip.

In a configuration, the discontinuity can comprise a fracture or a resection line.

In a configuration, the clip can be delivered such that the first elongate implant and the first leg of the clip and/or the second elongate implant and the second leg of the clip are separated by a distance.

In a configuration, the first and second elongate implants can be delivered prior to delivering the clip.

In a configuration, the first and second elongate implants can be delivered after delivering the clip.

In a configuration, the clip can be in a deformed configuration when the first and second elongate implants are delivered.

In a configuration, the first and second elongate implants can be delivered without crossing the discontinuity.

In a configuration, the clip can be delivered without the first and/or second legs crossing the discontinuity.

In a configuration, the method can further comprise positioning a clip drill guide across the discontinuity or joint, the clip drill guide comprising a first cannula positioned on the first side of the discontinuity or joint, and a second cannula positioned on the second side of the discontinuity or joint; drilling a first clip leg hole through the first cannula; inserting a first temporary pin through the first cannula and into the first clip leg hole; drilling a second clip leg hole through the second cannula; inserting a second temporary pin through the second cannula and into the second clip leg hole; positioning an implant guide on the first side of the discontinuity or joint by sliding one of a plurality of guide positioning holes running through the implant guide over the first temporary pin; forming a first implant hole by inserting a hole creation device through one of a plurality of implant positioning holes running through the implant guide, wherein the plurality of implant positioning holes can be positioned closer to the discontinuity or joint than the plurality of guide positioning holes; positioning the implant guide on the second side of the discontinuity or joint by sliding the one or another one of the plurality of guide positioning holes over the second temporary pin; forming a second implant hole by inserting the hole creation device or a second hole creation device through the one or another one of the plurality of implant positioning holes; inserting the first implant into the first implant hole; inserting the second implant into the second implant hole; removing the first and second temporary pins; and inserting the first leg of the clip into the first clip leg hole and inserting the second leg of the clip into the second clip leg hole.

In a configuration, the hole creation device can comprise a drill bit.

In a configuration, the hole creation device can comprise a bone punch.

In a configuration, the method can further comprise positioning a first drill guide across the discontinuity or joint, the first drill guide comprising a first cannula positioned on the first side of the discontinuity or joint, and a second cannula positioned on the second side of the discontinuity or joint; drilling a first clip leg hole through the first cannula; inserting a first temporary pin through the first cannula and into the first clip leg hole; drilling a second clip leg hole through the second cannula; inserting a second temporary pin through the second cannula and into the second clip leg hole; positioning an implant guide on the first side of the discontinuity or joint by sliding one of a plurality of guide positioning holes running through the implant guide over the first temporary pin; inserting a first implant guide wire through one of a plurality of implant positioning holes can be through the implant guide, wherein the plurality of implant positioning holes are positioned closer to the discontinuity or joint than the plurality of guide positioning holes; positioning the implant guide on the second side of the discontinuity or joint by sliding the one or another one of the plurality of guide positioning holes over the second temporary pin; inserting a second implant guide wire through the one or another one of the plurality of implant positioning holes; inserting the first implant over the first implant guide wire and into the bone or bone portion; inserting the second implant over the second implant guide wire and into the bone or bone portion; removing the first and second implant guide wires; removing the first and second temporary pins; and inserting the first leg of the clip into the first clip leg hole and inserting the second leg of the clip into the second clip leg hole.

In a configuration, the plurality of implant positioning holes can be of smaller diameter than the plurality of guide positioning holes.

In a configuration, the implant guide can be arc-shaped, the plurality of implant positioning holes passing through the implant guide at varying angles and the plurality of guide positioning holes passing through the implant guide at varying angles.

In the present disclosure, an example method of fixing bone portions defined by a discontinuity in a bone or fixing two bones across a joint can comprise delivering at least one elongate implant into a bone or bone portion on a first side of the discontinuity or joint; and delivering a clip into the bones or bone portions, a first leg of the clip on the first side of the discontinuity or joint, a second leg of the clip on the second side of the discontinuity or joint, and a bridge connecting first ends of the first and second legs extending across the discontinuity or joint, wherein the clip can be biased to be in a first configuration and wherein the clip can be delivered in a second deformed configuration such that a distance between free ends of the first and second legs of the clip is increased relative to the first configuration, wherein the at least one elongate implant can be positioned between the first leg of the clip and the discontinuity or joint, and wherein the at least one elongate implant can be at an angle with the first leg of the clip.

In a configuration, the method can further comprise pre-drilling holes in the bone or bone portions, the holes configured to receive the at least one elongate implant and/or the first and second legs of the clip.

In a configuration, the pre-drilling can comprise using a clip drill guide to locate the holes for the first and second legs of the clip.

In a configuration, the pre-drilling can comprise using an implant guide to locate the hole for the at least one elongate implant.

In a configuration, the clip drill guide and the implant guide can comprise an integral device.

In a configuration, the implant guide can comprise a plurality of holes for selection of the angle.

In a configuration, the plurality of holes can comprise holes sized for delivery of a non-cannulated screw.

In a configuration, the at least one elongate implant can comprise a non-cannulated screw.

In a configuration, the plurality of holes can comprise holes sized for a k-wire configured to deliver of a cannulated screw.

In a configuration, the at least one elongate implant can comprise a cannulated screw.

In a configuration, the holes for the at least one elongate implant can be offset from the holes to locate the first leg by a distance.

In a configuration, the at least one elongate implant can have a length such that the at least one elongate implant is configured to achieve bicortical purchase.

In a configuration, the at least one elongate implant can be delivered so that the leading end of the at least one elongate implant protrudes from an outer surface of the bone or bone portions.

In a configuration, the discontinuity can comprise a fracture or a resection line.

In a configuration, the clip can be delivered such that the at least one elongate implant and the first leg of the clip is separated by a distance.

In a configuration, the at least one elongate implant can be delivered prior to delivering the clip.

In a configuration, the first and second elongate implants can be delivered after delivering the clip.

In a configuration, the clip can be in a deformed configuration when the first and second elongate implants are delivered.

In a configuration, the at least one elongate implant can be delivered without crossing the discontinuity.

In a configuration, the clip can be delivered without the first and/or second legs crossing the discontinuity.

In a configuration, the method can further comprise positioning a clip drill guide across the discontinuity or joint, the clip drill guide comprising a first cannula positioned on the first side of the discontinuity or joint, and a second cannula positioned on the second side of the discontinuity or joint; drilling a first clip leg hole through the first cannula; inserting a first temporary pin through the first cannula and into the first clip leg hole; drilling a second clip leg hole through the second cannula; inserting a second temporary pin through the second cannula and into the second clip leg hole; positioning an implant guide on the first side of the discontinuity or joint by sliding one of a plurality of guide positioning holes running through the implant guide over the first temporary pin; forming an implant hole by inserting a hole creation device through one of a plurality of implant positioning holes running through the implant guide, wherein the plurality of implant positioning holes can be positioned closer to the discontinuity or joint than the plurality of guide positioning holes; inserting the at least one elongate implant into the implant hole; removing the first and second temporary pins; and inserting the first leg of the clip into the first clip leg hole and inserting the second leg of the clip into the second clip leg hole.

In a configuration, the hole creation device can comprise a drill bit.

In a configuration, the hole creation device can comprise a bone punch.

In a configuration, the method can further comprise positioning a first drill guide across the discontinuity or joint, the first drill guide comprising a first cannula positioned on the first side of the discontinuity or joint, and a second cannula positioned on the second side of the discontinuity or joint; drilling a first clip leg hole through the first cannula; inserting a first temporary pin through the first cannula and into the first clip leg hole; drilling a second clip leg hole through the second cannula; inserting a second temporary pin through the second cannula and into the second clip leg hole; positioning an implant guide on the first side of the discontinuity or joint by sliding one of a plurality of guide positioning holes running through the implant guide over the first temporary pin; inserting an implant guide wire through one of a plurality of implant positioning holes running through the implant guide, wherein the plurality of implant positioning holes can be positioned closer to the discontinuity or joint than the plurality of guide positioning holes; inserting the at least one elongate implant over the implant guide wire and into the bone or bone portion; removing the implant guide wire; removing the first and second temporary pins; and inserting the first leg of the clip into the first clip leg hole and inserting the second leg of the clip into the second clip leg hole.

In a configuration, the plurality of implant positioning holes can be of smaller diameter than the plurality of guide positioning holes.

In a configuration, the plurality of implant positioning holes can be sized to receive a guide tube, and the guide tube can be configured to slidably receive the implant guide wire.

In a configuration, the implant guide can be arc-shaped, the plurality of implant positioning holes passing through the implant guide at varying angles and the plurality of guide positioning holes passing through the implant guide at varying angles.

The foregoing summary is illustrative only and is not intended to be limiting. Other aspects, features, and advantages of the systems, devices, and methods and/or other subject matter described in this application will become apparent in the teachings set forth below. The summary is provided to introduce a selection of some of the concepts of this disclosure. The summary is not intended to identify key or essential features of any subject matter described herein.

BRIEF DESCRIPTION OF THE DRAWINGS

Various examples are depicted in the accompanying drawings for illustrative purposes, and should in no way be interpreted as limiting the scope of the examples. Various features of different disclosed examples can be combined to form additional examples, which are part of this disclosure.

FIGS. 11A-11E illustrate certain steps using an alternative drill guide for implanting the fixation system of FIGS. 3A-5C.

DETAILED DESCRIPTION

The various features and advantages of the systems, devices, and methods of the technology described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/or substituted as will be apparent to those of ordinary skill in the art upon consideration of the principles disclosed herein.

Overview of Bone Fixation System Examples

This disclosure describes improved systems and methods for stabilizing bones or bone fragments intended to be fused together, while applying a therapeutic level of continuous mechanical load or stress across the discontinuity.

A bone staple or clip can exert a compressive force between two bone portions to aid in at least stabilizing the two bone portions to promote healing at a discontinuity in the bone portions. In a bone fixation system disclosed herein, additional implant(s) can be used in combination with the clip to further increase fixation strength of the system in the bone portions, and/or improve healing of the fixed bone portions. When the additional implant(s) are implanted with the clip on opposite sides of the discontinuity (and without crossing the discontinuity in some embodiments), at an angle with legs of the clip, and adjacent (for example, immediately adjacent) the legs of the clip, the crossing of the additional implant(s) and the legs of the clip can improve cortical purchase of the fixation system. The compressive force exerted by the legs of the clip toward each other can be transmitted to the more transversely inserted fixation devices to apply a more evenly distributed compressive force across the discontinuity.

As will be described in greater detail below, the additional implant(s) can include one or more screws, for example, fixation screws or compression screws, which can be cannulated or non-cannulated, fully threaded or partially threaded, and/or can include a driver head or be headless. In some implementations, a fixation plate can be used with the screws. In other implementations, the additional implant(s) can include a second clip that is implanted at an angle to the first clip so that the legs of the first and second clips are crossed when viewed from a side looking into the plane of discontinuity. The second clip can have the same features as the first clip or different features.

Figure 1:
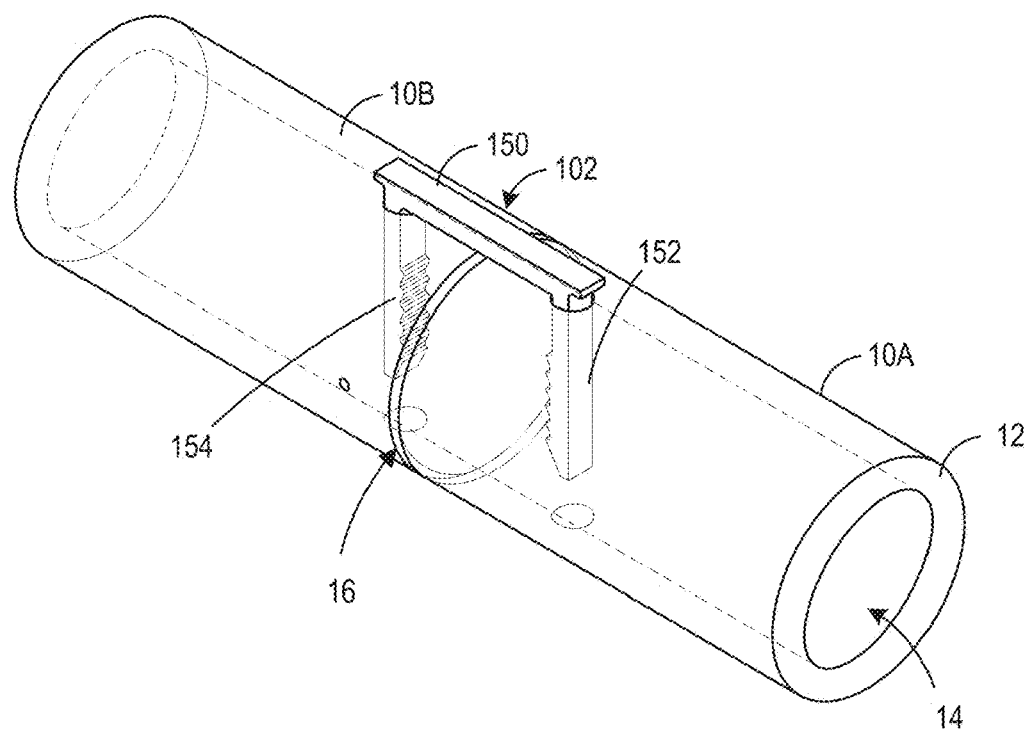
FIG. 1 is a perspective view of example bone portions, which are schematic representations, and a fixation device implanted across a boundary in the bone portions.

Referring to FIG. 1, an example bone staple or clip 102 can be used to stabilize two bone portions 10A, 10B that are separated, partially or entirely, at a boundary or discontinuity 16. For example, the discontinuity 16 can be a fracture site, a resection site, or other bone-to-bone interfaces. The bone portions 10A, 10B can be part of the same bone or different bones prior to the formation of the discontinuity 16. The clip 102 can be made of titanium, stainless steel, polyether ether ketone (PEEK), nitinol, and/or other rigid or semi-rigid biocompatible materials or combinations thereof.

As shown in FIGS. 2A-2E, the clip 102 can be formed as an integral piece. In some embodiments, the clip can include a material, such as nitinol, or other shape-memory material(s). The clip 102 can include bone engaging legs 152, 154, which can be referred to as members or prongs. The bone engaging legs 152, 154 can be connected by a bridge 150. The bone engaging leg 152 extends from near a first end of the bridge 150. The bone engaging leg 152 can include a first end attached to the bridge 150 and a second end, which can be a free end. The bone engaging leg 152 can have a substantially uniform thickness substantially along its entire length. In other implementations, the bone engaging leg 152 can be tapered towards the free end. The bone engaging leg 154 extends from near a second end of the bridge 150. The bone engaging leg 154 can include a first end attached to the bridge 150 and a second end, which can be a free end. The bone engaging leg 154 can have a substantially uniform thickness substantially along its entire length. In other implementations, the bone engaging leg 154 can be tapered towards the free end. The bone engaging legs 152, 154 can include teeth 153, 155 respectively, or other grip-enhancement features. The teeth 153, 155 can improve bone purchase and/or improve pull out strength of the clip 102 from the bone portions 10A, 10B shown in FIG. 1. The teeth 153 and the teeth 155 can face each other. In other implementations, the teeth 153, 155 can be on any one or more longitudinally or substantially longitudinally extending surfaces of the bone engaging legs 152, 154.

The bridge 150 can include first and second shoulders 156, 158 on opposite ends thereof. The shoulders 156, 158 can extend away from connection locations for the legs 152, 154 along a longitudinal axis of the bridge 150 (which can be generally transverse to a central longitudinal axis of the clip 102) to terminate at free ends of the bridge 150, respectively. In some implementations, the shoulders 156, 158 can include tabs, ears, protrusions, wings, retainers, or other retaining members. Alternatively, the shoulders 156, 158 can extend along a generally transverse direction to the longitudinal axis of the bridge 150. In some embodiments, the bridge 150 can be symmetrical about the central longitudinal axis of the clip 102.

Figure 2A:
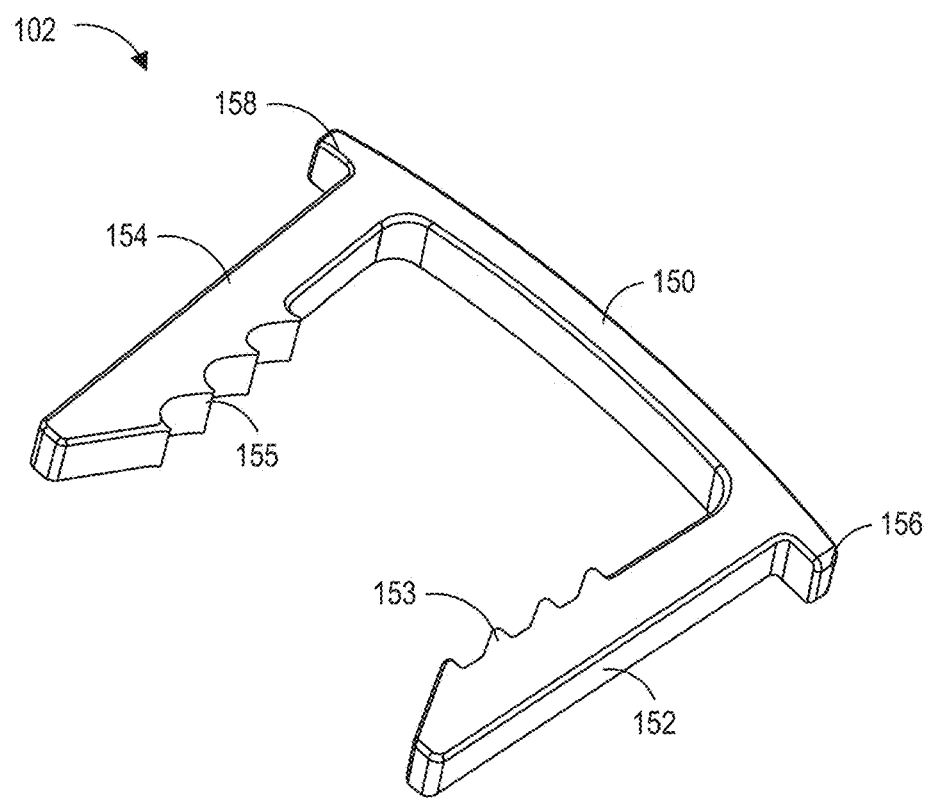
FIG. 2A is a perspective view of the fixation device in FIG. 1.
Figure 2B:
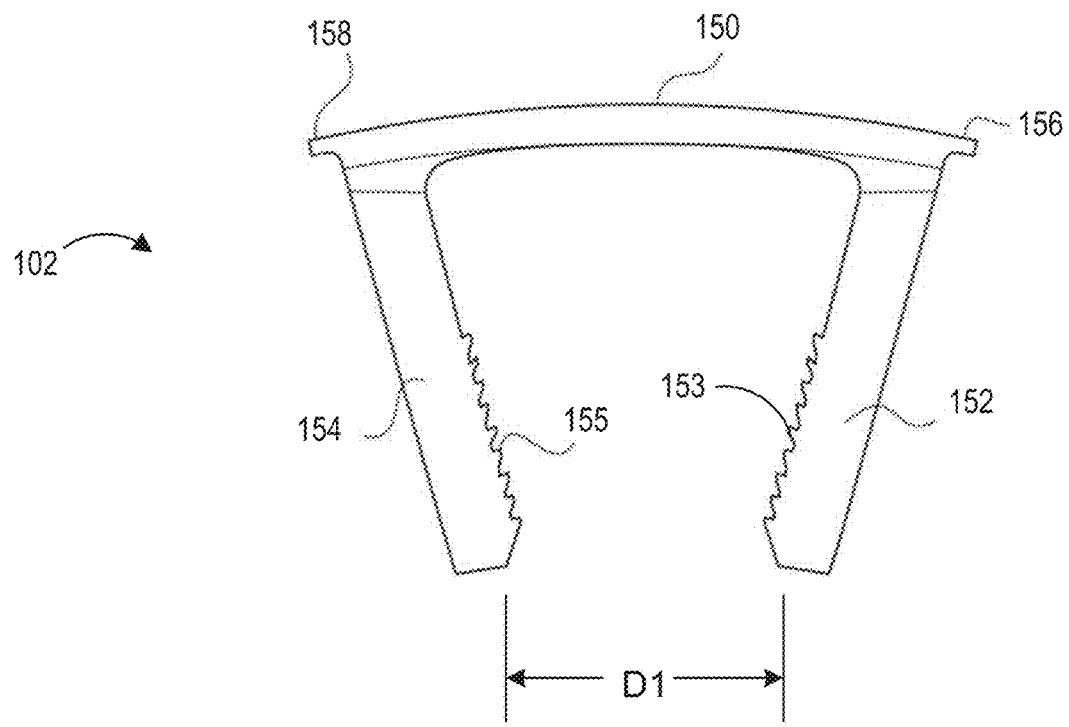
FIG. 2B is a view of the fixation device in FIG. 1 in a free configuration.
Figure 2C:
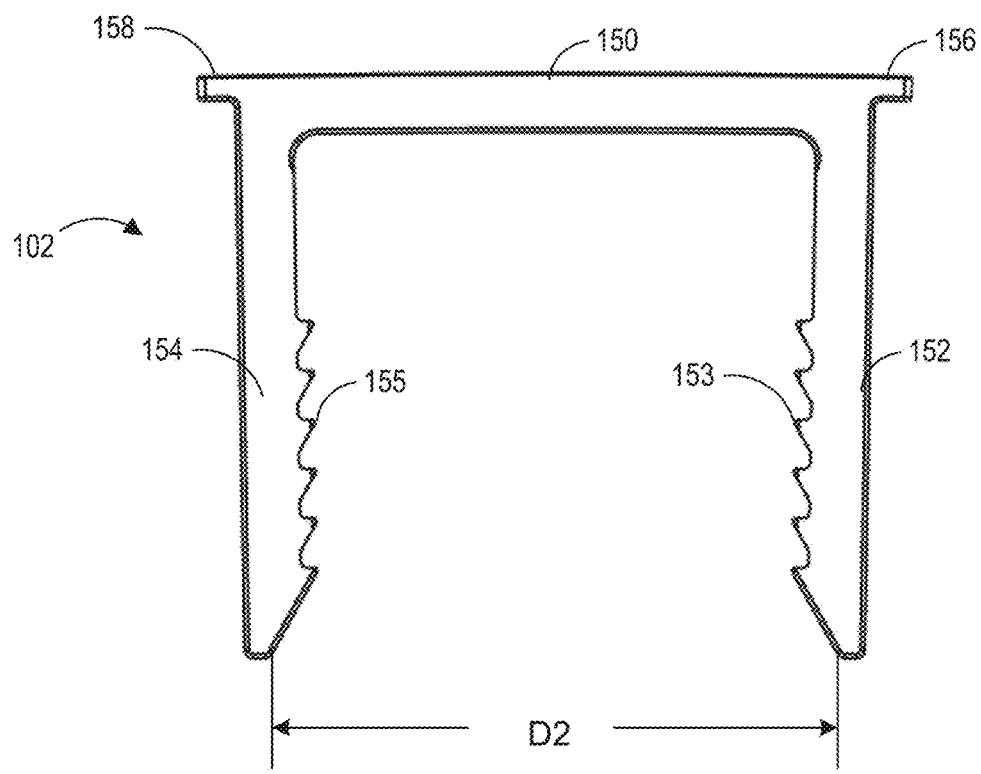
FIG. 2C is a view of the fixation device in FIG. 1 in a deformed configuration.
Figure 2D:
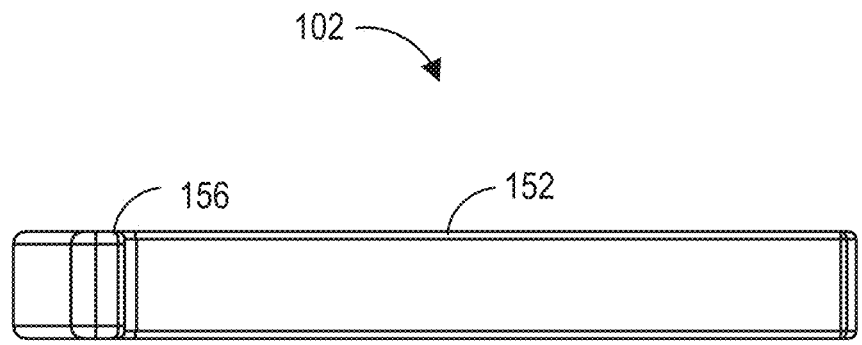
FIG. 2D is a side view of the fixation device in FIG. 1 in the free configuration.
Figure 2E:
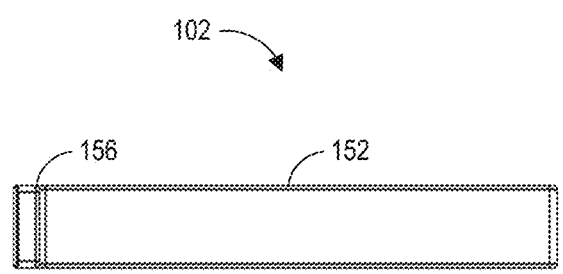
FIG. 2E is a side view of the fixation device in FIG. 1 in the deformed configuration.

As described further in U.S. Pat. App. No. 2018/0317906 (the entirety of which is hereby incorporated by reference herein and should be considered part of the disclosure), the clip 102 can change between a free configuration and a deformed configuration. When free from a net external force, the clip 102 can be in a free configuration, such as shown in FIG. 2B. In other words, the clip 102 can be biased in the free configuration. In the free configuration, the bridge 150 can have a curvature with a concave side facing the legs 152, 154. The free ends of the legs 152, 154 can be separated by a first distance D1 in the free configuration as shown in FIG. 2B. A force can be exerted to change, for example, reduce or otherwise, the curvature of the bridge 150 so that the clip 102 can be deformed, such as shown in FIGS. 2C and 2E. In the fully deformed configuration, the bridge 150 is elastically straightened. As shown in FIG. 2C, the free ends of the bone engaging leg 152, 154 are spaced further apart to a second distance D2 that is greater than D1 in the free configuration.

Figure 2F:
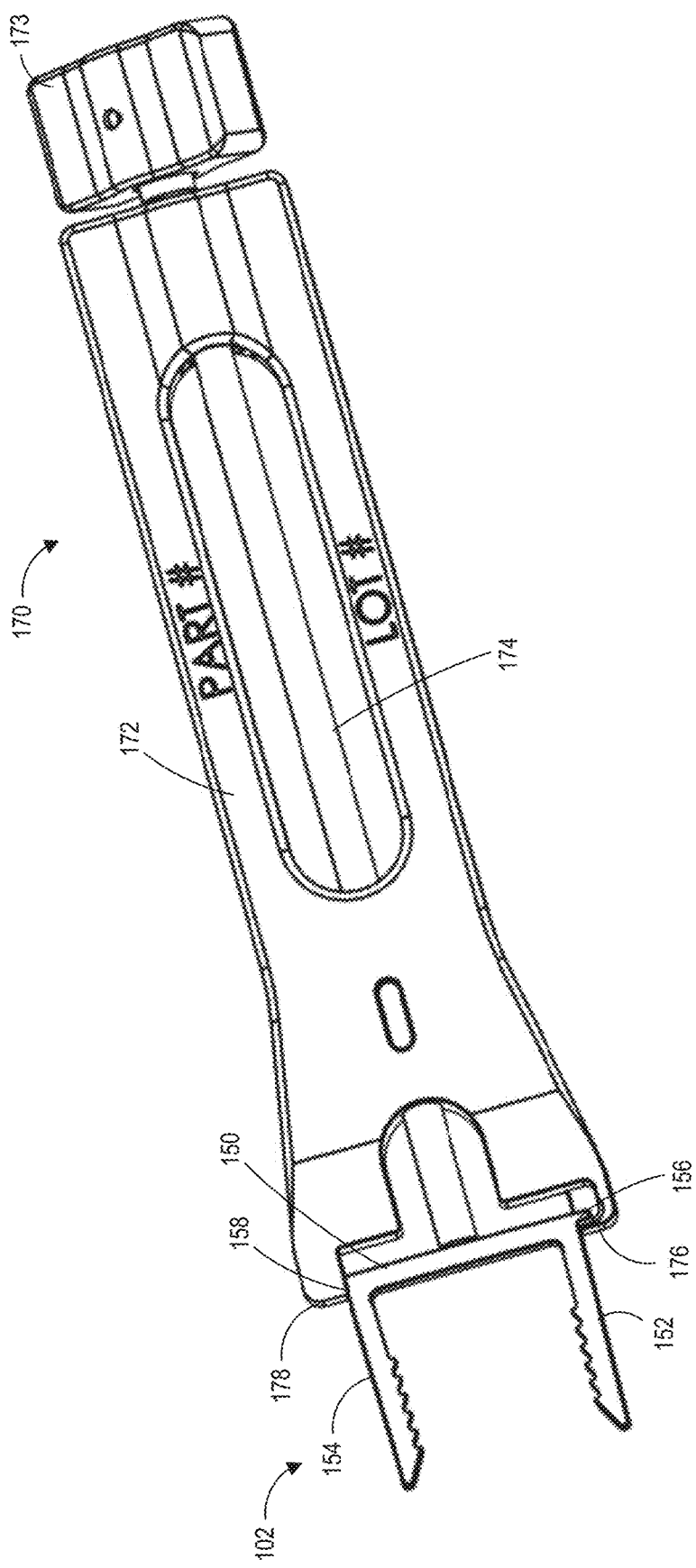
FIG. 2F is a perspective view of an example inserter tool coupled to the fixation device in FIG. 1.

The clip 102 can be movable between the free configuration and the deformed configuration by an inserter tool 170, such as shown in FIG. 2F. The inserter tool 170 can include a body 172, and a knob 173. The knob 173 can be at a proximal end of the inserter tool 170. An at least partially threaded shaft 174 can have a first end that is connected with the knob 173 and a second, free, end at or near a distal end of the inserter tool 170. The shaft 174 can be movable along a longitudinal axis of the inserter tool 170 by rotation of the knob 173. The inserter tool 170 can include a pair of jaws 176, 178 at its distal end, near or adjacent to second, free, end of the shaft 174. The bridge 150 of the clip 104 can be placed between the jaws 176, 178. The shoulders 156, 158 of the clip 104 can engage within the respective members of the pair of jaws 176, 178. The second, free, end of the shaft 174 can engage with the bridge 150. By translation of the shaft 174 axially against the bridge 150 and securement of the shoulders 156, 158 within the jaws 176, 178, the bridge 150 can be flexed or straightened between the free configuration and the deformed configuration.

Referring back to FIG. 1, the bone engaging legs 152, 154 of the clip 102 can have a length such that the free ends of the bone engaging legs 152, 154 are configured to terminate in a cancellous bone region 14 of the bone portions 10A, 10B, and another portion of the bone engaging legs 152, 154 are configured to engage a cortical bone region 12 on one side of the bone portions 10A, 10B. As shown, the clip 102 may not engage the cortical bone region on the radially opposite side of the bone portions 10A, 10B. Fixation in the cancellous bone region is not as strong as fixation in the cortical bone region. The cortical and cancellous bone regions are not illustrated in subsequent drawings including the schematic representation of the bone portions for clarity. In some embodiments, the bone engaging legs 152, 154 of the clip 102 can have a length such that at least one of the free ends of the bone engaging legs 152, 154 achieves bicortical purchase.

Figure 3A:
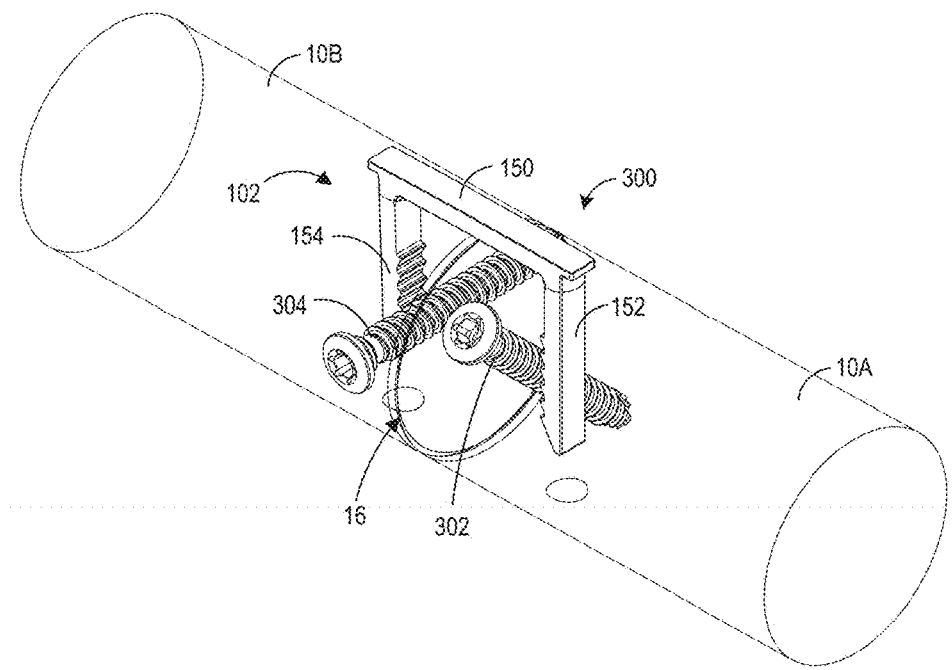
FIG. 3A is a perspective view of example bone portions, which are schematic representations, and a fixation system including the fixation device in FIG. 1 implanted across a discontinuity in the bone portions and a plurality of screws implanted on opposite sides of the discontinuity.
Figure 3B:
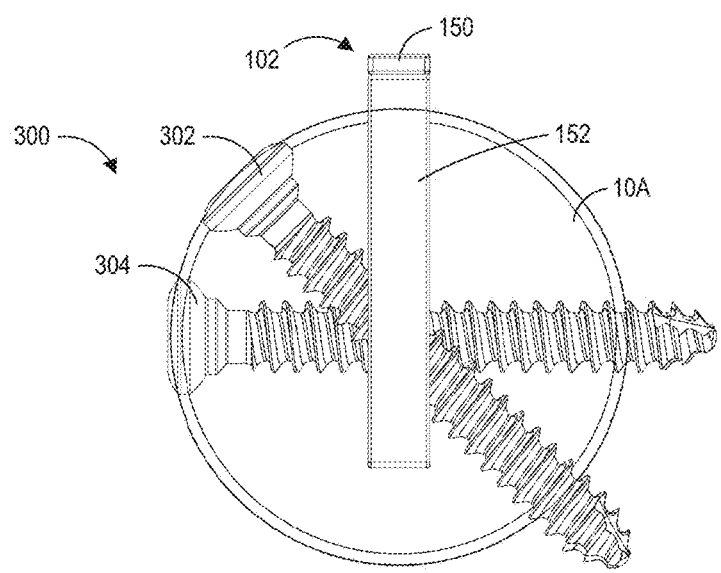
FIG. 3B is a side view of the bone portions and the fixation system of FIG. 3A.

FIGS. 3A and 3B illustrate an example fixation system 300 that can improve fixation of the fixation system 300 in the cortical bone region and/or healing of the bone portions 10A, 10B. The fixation system 300 can include the clip 102 in the deformed configuration and one or more (for example, two) screws 302, 304. In some implementations, the screws 302, 304 can be compression screws, which has its plain and ordinary meaning as understood by a person of ordinary skill in the art. The screws 302, 304 can be non-cannulated. The screws 302, 304 can be threaded along substantially its entire shaft length. The screws 302, 304 can have a length configured to achieve bicortical purchase in the bone portions 10A, 10B. As shown in FIG. 3B, leading ends of the screws 302, 304 can protrude slightly from an outer surface of the bone portions 10A, 10B. In other embodiments, the leading ends of the screws do not protrude from the cortical surface of the bone. The term "bicortical purchase" has its plain and ordinary meaning as understood by a person of ordinary skill in the art. The length of the screws 302, 304 may or may not be longer than the length of the legs 152, 154 of the clip 102.

As shown in FIG. 3A, the screw 302 can be on the same side of the discontinuity 16 as the bone engaging leg 152 and the screw 304 can be on the same side of the discontinuity 16 of the bone engaging leg 154. The bridge 150 of the clip 102 can span across the discontinuity 16. The screw 302 is between the discontinuity 16 and the bone engaging leg 152. The screw 304 is between the discontinuity 16 and the bone engaging leg 154. Preferably, there can be interference between the bone engaging leg 152 and the screw 302 and/or between the bone engaging leg 154 and the screw 304. Optionally, the screws 302, 304 can be separated from the bone engaging legs 152, 154 respectively by a gap. The size of the gap can be varied. The spacing of the screw 302, 304 relative to the leg 152, 154 can be anywhere from interference to about a 2-mm gap. The spacing can be at least partially based on the length and/or the convergence angle of the legs 152, 154, which can be used to determine the amount of movement the legs 152, 154 has before benefiting from contacting the screw 302, 304.

As shown in FIGS. 3A and 3B, the screw 302 can be at a first angle to the bone engaging leg 152 and the screw 304 can be at a second angle to the bone engaging leg 154. The first and second angles can be the same or different. The respective angles between the screws 302, 304 and the bone engaging legs 152, 154 can be varied, for example, depending on the adjacent anatomy, the surgical exposure, and/or otherwise. In some embodiments, the screws 302, 304, and the bone engaging legs 152, 154 of the clip 102 do not cross the discontinuity. Not extending across the discontinuity 16 can be advantageous in bone fusion procedures, where the amount of space, particularly cortical bone space, available for a fixation device, such as a compression screw, at the discontinuity 16 (such as a fracture line) is limited. In some implementations, the screws 302, 304, and/or the bone engaging legs 152, 154 are implanted generally transverse to the bone portions 10A, 10B.

The compressive force (due to the deformation of the bridge 150 of the clip 102) between the bone engaging legs 152, 154, which terminate in the cancellous bone region, can be transmitted to the screws 302, 304 therebetween, which have bicortical purchase and are at an angle with the legs 152, 154. The combination can result in more contact between the fixation system 300 and the cortical region of the bone portions 10A, 10B. The screws 302, 304 can facilitate in more evenly distributing the compressive force provided by the bone engaging legs 152, 154 of the clip 102 across the discontinuity 16. The fixation system 300 can thereby result in greater fixation strength and/or promote greater stabilization of the bone portions 10A, 10B.

Figure 4A:
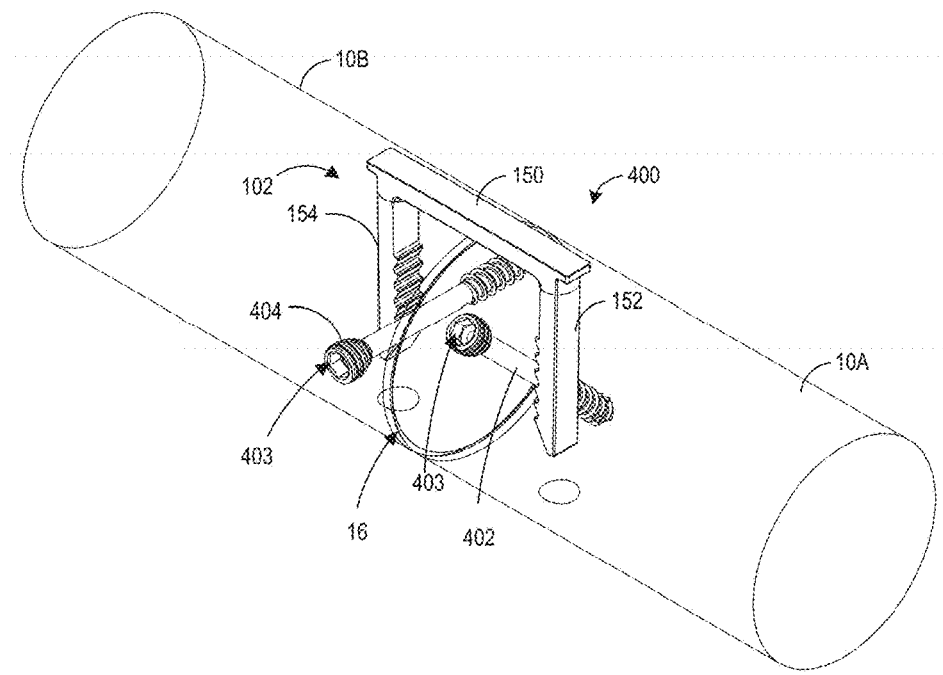
FIG. 4A is a perspective view of example bone portions, which are schematic representations, and another fixation system including the fixation device in FIG. 1 implanted across a discontinuity in the bone portions and a plurality of cannulated screws implanted on opposite sides of the discontinuity.
Figure 4B:
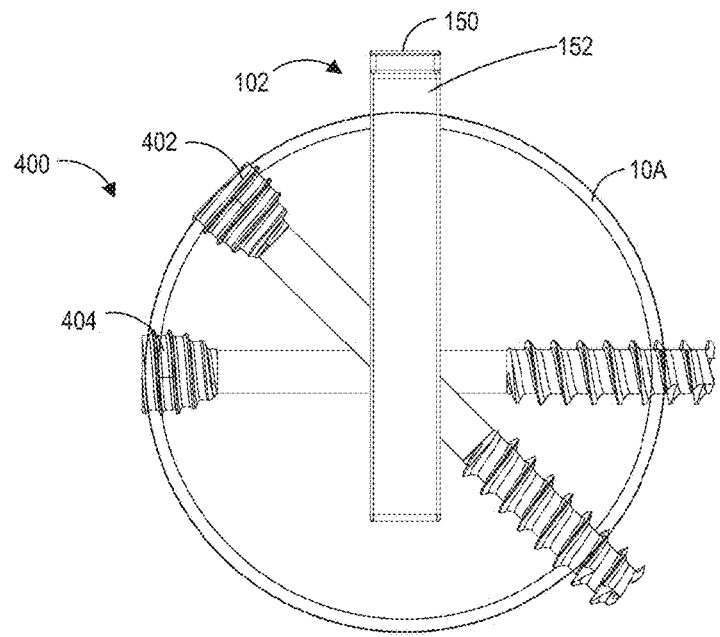
FIG. 4B is a side view of the bone portions and the fixation system of FIG. 4A.
Figure 5A:
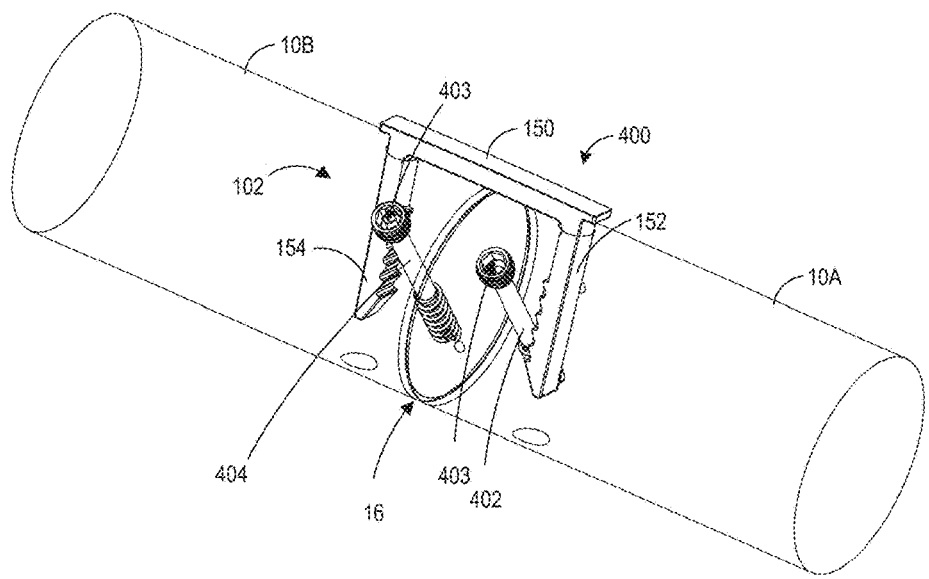
FIG. 5A is a perspective view of example bone portions, which are schematic representations, and the fixation system of FIGS. 4A-4B with different insertion angles of the cannulated screws than as shown in FIGS. 4A-4B.
Figure 5B:
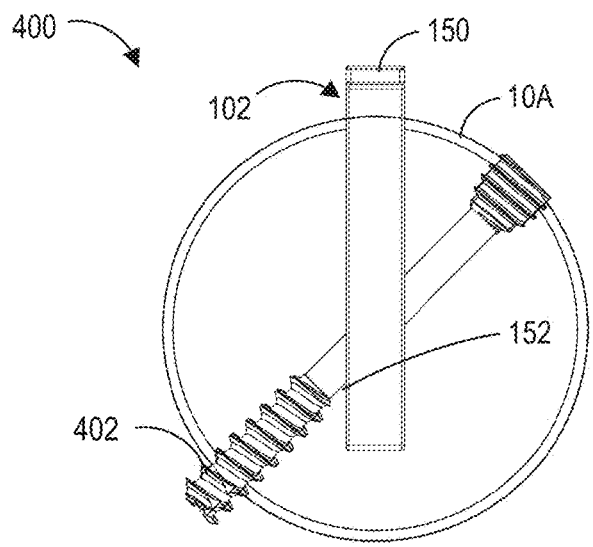
FIG. 5B is a side view of the bone portions and the fixation system of FIG. 5A.
Figure 5C:
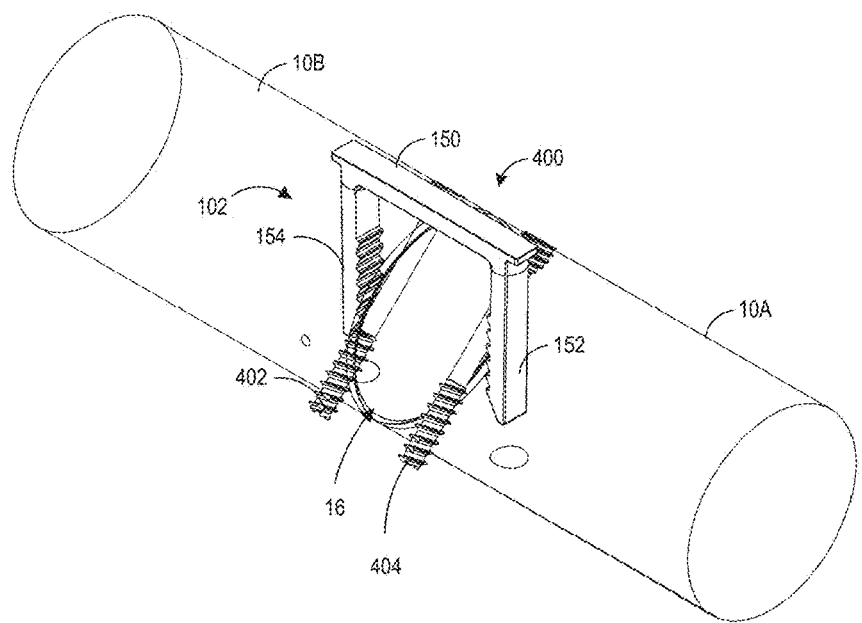
FIG. 5C is another perspective view of the bone portions and the fixation system of FIG. 5A.

FIGS. 4A-4B and 5A-5B illustrate an example fixation system 400 that can improve fixation of the system 400 in the cortical bone region and/or healing of the bone portions 10A, 10B. The system 400 can include the clip 102 in the deformed configuration and one or more (for example, two) screws 402, 404. In some implementations, the screws 402, 404 can be compression screws. The screws 402, 404 can be cannulated, including a channel 403 configured to receive a k-wire. The screws 402, 404 can be threaded along a portion of its shaft length. The threads can extend from the leading end of the screws 402, 404 toward its trailing end or its driver head. The screws 402, 404 can have a length configured to achieve bicortical purchase in the bone portions 10A, 10B. As shown in FIGS. 4B and 5B, leading ends of the screws 402, 404 can protrude slightly from an outer surface of the bone portions 10A, 10B. In other embodiments, the leading ends of the screws do not protrude from the cortical surface of the bone. The length of the screws 302, 304 may or may not be longer than the length of the legs 152, 154 of the clip 102.

As shown in FIGS. 4A and 5A, the screw 402 can be on the same side of the discontinuity 16 as the bone engaging leg 152 and the screw 404 can be on the same side of the discontinuity 16 of the bone engaging leg 154. The bridge 150 of the clip 102 can span across the discontinuity 16. The screw 402 is between the discontinuity 16 and the bone engaging leg 152. The screw 404 is between the discontinuity 16 and the bone engaging leg 154. Preferably, there can be interference between the bone engaging leg 152 and the screw 402 and/or between the bone engaging leg 154 and the screw 404. Optionally, the screws 402, 404 can be separated from the bone engaging legs 152, 154 respectively by a gap. The size of the gap can be varied. The spacing of the screw 402, 404 relative to the leg 152, 154 can be anywhere from interference to about a 2-mm gap. The spacing can be at least partially based on the length and/or the convergence angle of the legs 152, 154, which can be used to determine the amount of movement the legs 152, 154 has before benefiting from contacting the screw 402, 404.

As shown in FIGS. 4A and 4B, the screw 402 can be at a first angle to the bone engaging leg 152 and the screw 404 can be at a second angle to the bone engaging leg 154. The first and second angles can be different. As shown in FIGS. 5A and 5B, the screws 402, 404 can be at substantially the same angle with respect to the bone engaging legs 152. 154. The screws 402, 404 can be substantially parallel. In the implementation such as shown in FIGS. 5A-5B, the system 400 can be substantially symmetrical about the plane of the discontinuity 16. The respective angle(s) between the screws 402, 404 and the bone engaging legs 152, 154 can be varied, for example, depending on the adjacent anatomy, the surgical exposure, and/or otherwise.

In some embodiments, the screws 402, 404, and the bone engaging legs 152, 154 do not cross the discontinuity. Not extending across the discontinuity 16 can be advantageous in bone fusion procedures, where the amount of space, particularly cortical bone space, available for a fixation device, such as a compression screw, at the discontinuity 16 (such as a fracture line) is limited. In some implementations, the screws 402, 404, and/or the bone engaging legs 152, 154 are implanted generally transverse to the bone portions 10A, 10B.

The compressive force (due to the deformation of the bridge 150) between the bone engaging legs 152, 154, which terminates in the cancellous region, can be transmitted to the screws 402, 404 therebetween, which have bicortical purchase and are at an angle with the legs 152, 154. The combination can result in more contact between the fixation system 300 and the cortical region of the bone portions 10A, 10B. The screws 402, 404 can facilitate in more evenly distributing the compressive force provided by the bone engaging legs 152, 154 of the clip 102 across the discontinuity 16. The fixation system 400 can thereby result in greater fixation strength and/or promote faster healing of the bone portions 10A, 10B.

Figure 6:
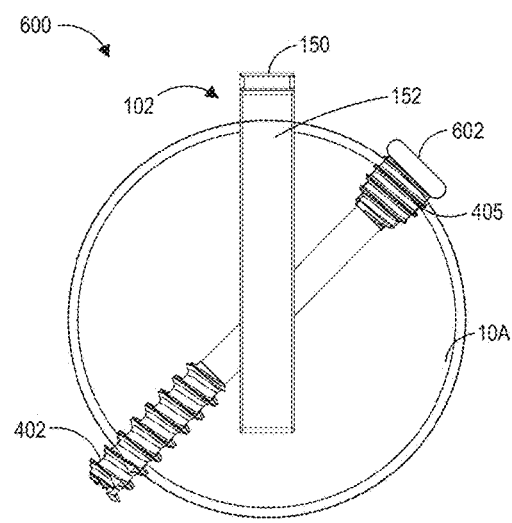
FIG. 6 is a side view of example bone portions, which are schematic representations, and a fixation system of FIGS. 5A-5B, and a fixation plate.

FIG. 6 illustrates an example fixation system 600 that can improve fixation of the system 600 in the cortical bone region and/or healing of the bone portions 10A, 10B. The fixation system 600 can incorporate any of the features of the system 400 described above. The system 600 can include the clip 102 in the deformed configuration, a plurality of (for example, two) the screws 402, 404, and a fixation plate 602. The screws 402 and 404 can include a driver head 405 that has an outer dimension greater than an outer diameter of the shaft of the screws. When the screws 402, 404 are implanted substantially parallel to each other, such as shown in FIG. 6, the heads 405 of the screws 402, 404 can engage with respective openings on the fixation plate 602. Alternatively, the screws 402, 404 can be implanted at an angle with each other and still between the bone engaging legs 152, 154 and on opposite sides of the discontinuity 16. The fixation plate 602 can improve bone reduction and therefore promote better fixation of the bone portions 10A, 10B.

Figure 7:
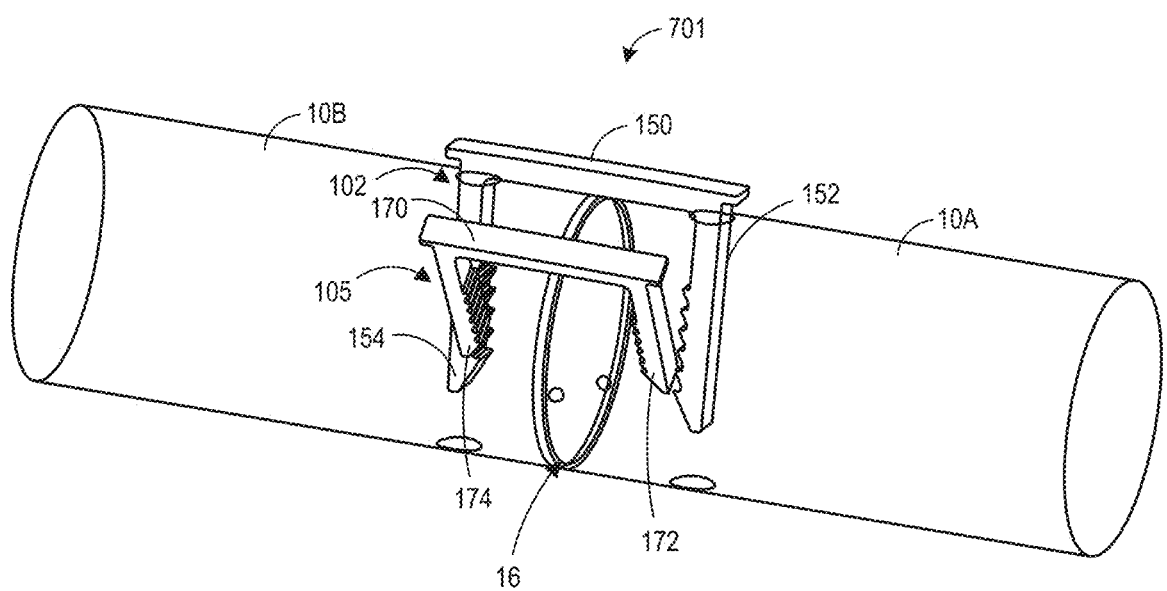
FIG. 7 is a perspective view of example bone portions, which are schematic representations, and a fixation system including two of the fixation device in FIG. 1 each implanted across a discontinuity in the bone portions.

FIG. 7 illustrates an example fixation system 700 that can improve fixation of the system 701 in the cortical bone region and/or healing of the bone portions 10A, 10B. The fixation system 701 can include a first clip 102 as described above (having elastic or superelastic properties) inserted in the deformed configuration and a substantially rigid second clip 105 (for example, that is not elastic). The legs 172, 174 of the second clip 105 may be substantially parallel or at another fixed angle relative to each other. The second clip 105 can have a shorter bridge 170 than the bridge 150 of the first clip 102. As shown in FIG. 7B, the bridges 150, 170 of the first and second clips 102, 105 each extend across the discontinuity 16. The bone engaging legs 172, 174 of the second clip 105 can be between the bone engaging legs 152, 154 of the first clip 102. The bone engaging legs 152, 154 of the first clip 102 can be at an angle to the bone engaging legs 172, 174 of the second clip 105. The respective angle(s) between the bone engaging legs 172, 174 and the bone engaging legs 152, 154 can be varied, for example, depending on the adjacent anatomy, the surgical exposure, and/or otherwise. In some embodiments, the bone engaging legs 152, 154 of the first clip 102 and the bone engaging legs 172, 174 of the second clip 105 do not cross the discontinuity 16. In some implementations, the bone engaging legs 152, 154 of the first clip 102 and/or the bone engaging legs 172, 174 of the second clip 105 are implanted generally transverse to the bone portions 10A, 10B. In some embodiments, the bone engaging legs 172, 174 of the second clip 105 are longer than the bone engaging legs 152, 154 of the first clip 102. In some embodiments, the bone engaging legs 172, 174 of the second clip 105 are long enough to achieve bi-cortical purchase.

In some embodiments, the compressive force (due to the deformation of the bridge 150) between the bone engaging legs 152, 154 of the first clip 102 can be transmitted to the rigid bone engaging legs 172, 174. The fixation of the bone engaging legs 172, 174 of the second clip 105 in the cortical region of the bone portions 10A, 10B is combined with the fixation of the bone engaging legs 152, 154 of the first clip 102 in the cortical region of the bone portions 10A, 10B to improve total cortical purchase. The combination can result in more contact between the fixation system 701 and the cortical region of the bone portions 10A, 10B and a greater and more evenly distributed compressive force across the discontinuity 16, thereby resulting in greater fixation strength and/or promote faster healing of the bone portions 10A, 10B.

The fixation system can include the clip 102 in the deformed configuration and other arrangements of additional implant(s) that are configured to increase cortical purchase of the system and/or intersect with the legs 152, 154 of the clip 102 to more evenly distribute the compressive force across the discontinuity 16, and/or to increase the compressive force across the discontinuity 16. For example, the additional implant(s) can include a cannulated screw and a non-cannulated screw, a plurality of nails, a plurality of pegs that are not threaded, a second bone staple that does not have a deformed configuration, or otherwise.

Example Tools and Methods of Implanting Certain Fixation Systems

Example methods of implanting the fixation systems 300, 400 as shown in FIGS. 3A-3B, 4A-B, and 5A-5C will be described below. A person of ordinary skill in the art will appreciate from this disclosure that the fixation systems disclosed herein can be implanted with other methods and/or delivery instruments. Not every step is illustrated here for brevity, although a person of ordinary skill in the art will appreciate that such steps can be included based on this disclosure. The methods and/or delivery instruments, entirely or partially, can also be used to deliver other examples of the fixation system.

Figure 8A:
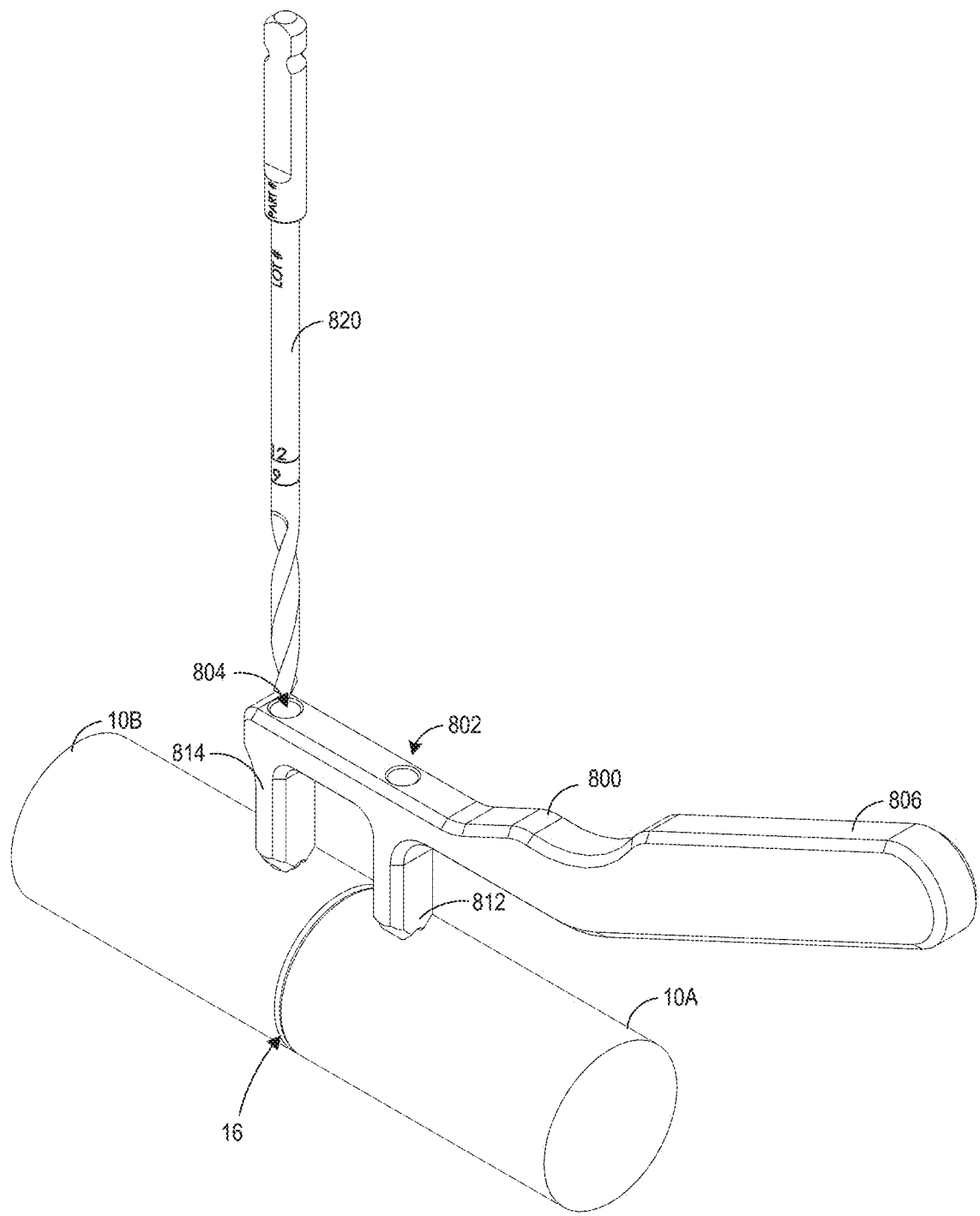
FIGS. 8A-8I illustrate certain steps for implanting the fixation system of FIGS. 3A-3B.

As shown in FIGS. 8A-8I, a method of fixing bone portions across a discontinuity using the fixation system 300 can include one or more of the following steps. As shown in FIG. 8A, a first drill guide 800 can be positioned across the discontinuity 16 against the outer surface of the bone portions 10A, 10B. The drill guide embodiments disclosed herein can aid in placing the screws in the appropriate location relative to the clip legs. The first drill guide 800 can include two locating openings 802, 804 configured to be placed against the bone portions 10A, 10B on opposite sides of the discontinuity 16. The openings 802, 804 can each extend into channels along posts 812, 814 respectively. The posts 812, 814 can have a predetermined length. In some implementations, the openings 802, 804 can be aligned to be generally transverse and/or symmetrically to the discontinuity 16. The first drill guide 800 can include a handle 806. The handle 806 can be aligned with a portion of the first drill guide 800 including the posts 812, 814. In some embodiments, the handle 806 can be angled relative to the portion of the first drill guide 800 including the posts 812, 814 to that portion to have easier access to the bone portions 10A, 10B, for example, when that portion needs to travel through a tight gap or a sharp corner in order to reach the bone portions 10A, 10B. The handle 806 can allow for easier placement of the locating openings 804, 806 relative to the outer surface of the bone portions 10A, 10B. The channels in the first drill guide 800 can receive and guide a hole creation device for creating a hole in bone. The hole creation device can include a drill bit, punch, reamer, broach, or other suitable device for making holes in bone.

Figure 8C:
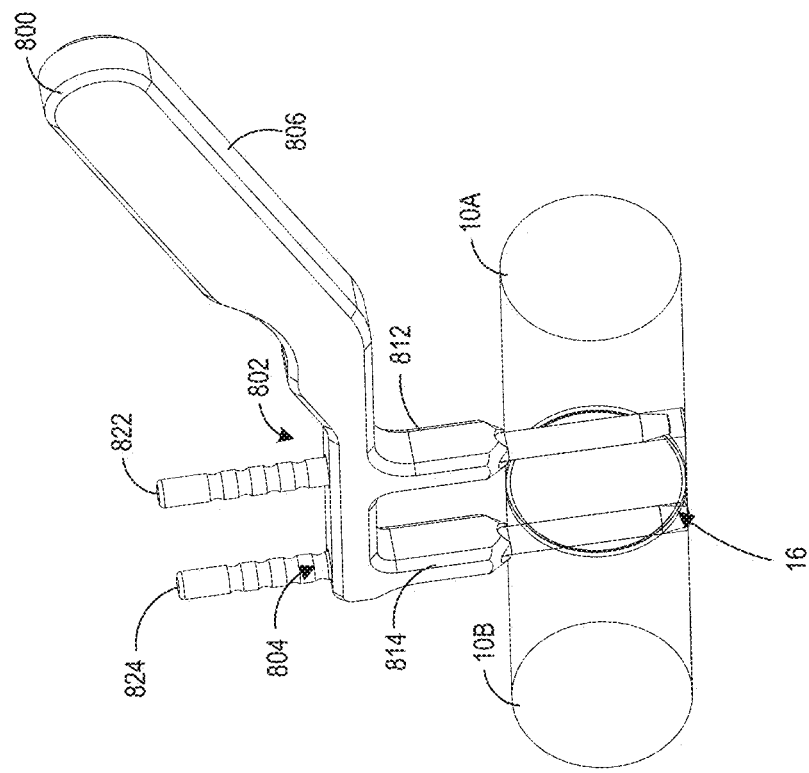
Figure 8B:
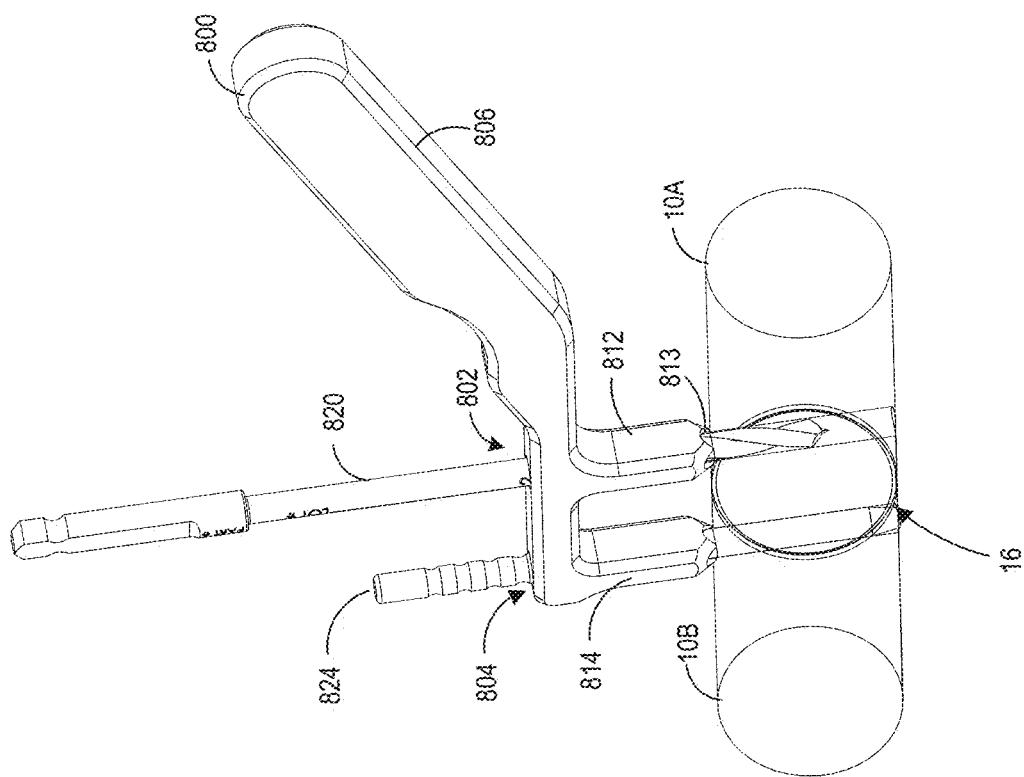
Figure 10A:
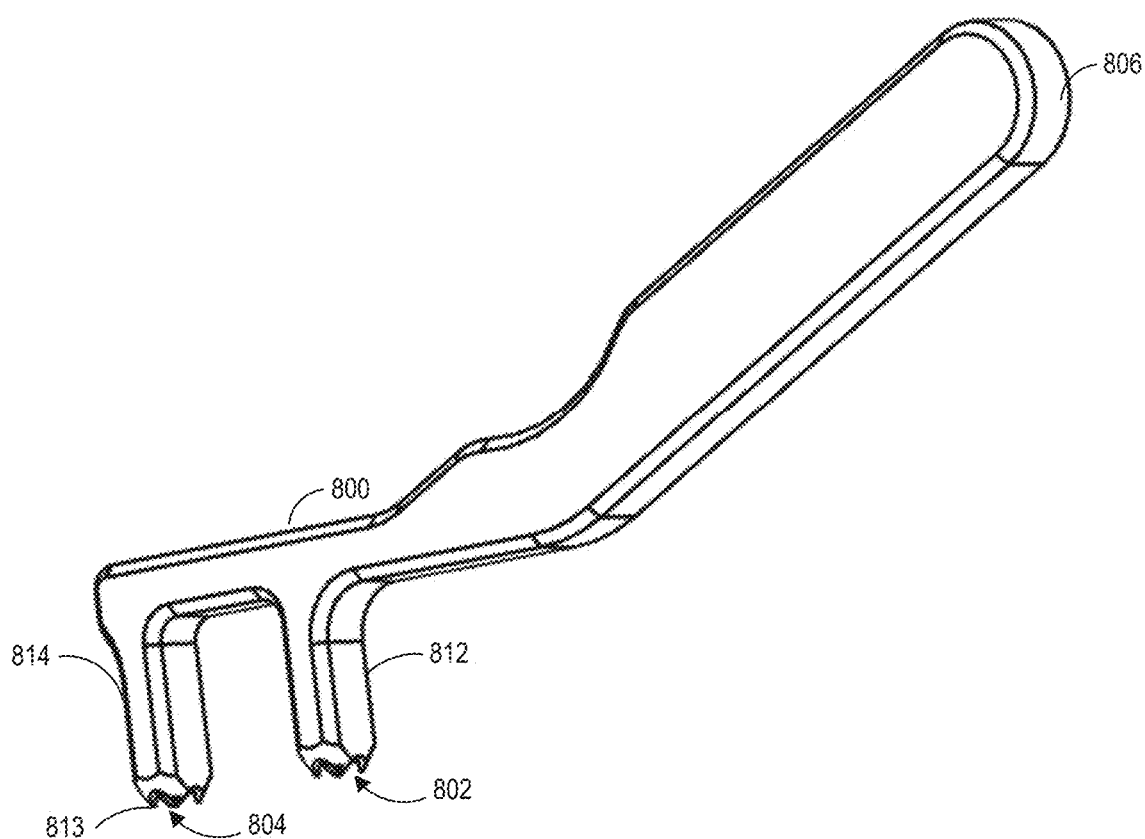
FIG. 10A illustrates a perspective view of an example drill guide for preparing bone portions for the implantation of the fixation device of FIGS. 2A-2D.

When a first reamer or drill bit 820 is inserted into one of the openings 802, 804 of the first drill guide 800, such as shown in FIGS. 8A and 8B, the length of the posts 812, 814 can be configured to guide the first drill bit 820 to travel in a line that extends through cortical regions on generally diametrically opposite sides of the bone portions 10A, 10B, although the first drill bit 820 needs not travel through the bone portions 10A, 10B to make a throughbore or a blind hole that is bicortical. Throughout this disclosure where a drill bit is shown as drilling a throughbore in the bone portion 10A, 10B, the drill bit can alternatively drill a closed hole. In some implementations, such as shown in FIGS. 8B-C, in which the bone portions 10A, 10B are illustrated as being transparent for clarity, the first drill bit 820 can drill a throughbore through the bone portions 10A, 10B. In other implementations, the first drill bit 820 can drill a blind hole through the bone portions 10A, 10B. The blind hole can have a depth such that the hole is bicortical or such that the hole terminates in a cancellous part of the bone. As shown in FIGS. 8B and 10A, the bone-contacting end of the posts 812, 814 can terminate in a plurality of tips 813 rather than a continuous ring. As shown in FIG. 8B, gaps between the tips 813 can allow visual confirmation of the first drill bit 820 making contact with the outer surface of the bone portions 10A, 10B.

As shown in FIG. 8B, after having created the hole in the bone portion 10B through the opening 804, a temporary fixation pin 824 can be inserted into the opening 804 of the first guide 800 and the bone portion 10B via the hole created by the first drill bit 820. The first drill bit 820 can then be used to create a bore as discussed above in the bone portion 10A via the opening 802 so that the temporary fixation pin 822 can be inserted into the opening 802 and into the bone portion 10A. As shown in FIG. 8C, temporary fixation pins 822, 824 can be inserted into the openings 802, 804 of the first drill guide 800 and into the holes (such as throughbores) in the bone portions 10A, 10B that are formed by the first drill bit 820. The temporary fixation pins 822, 824 can temporarily and removably couple a second drill guide 830 to one of the bone portions 10A, 10B, as described below. Each of the holes drilled by the first drill bit 820 can be sized to slidably receive a temporary fixation pin 822, 824.

Figure 8D:
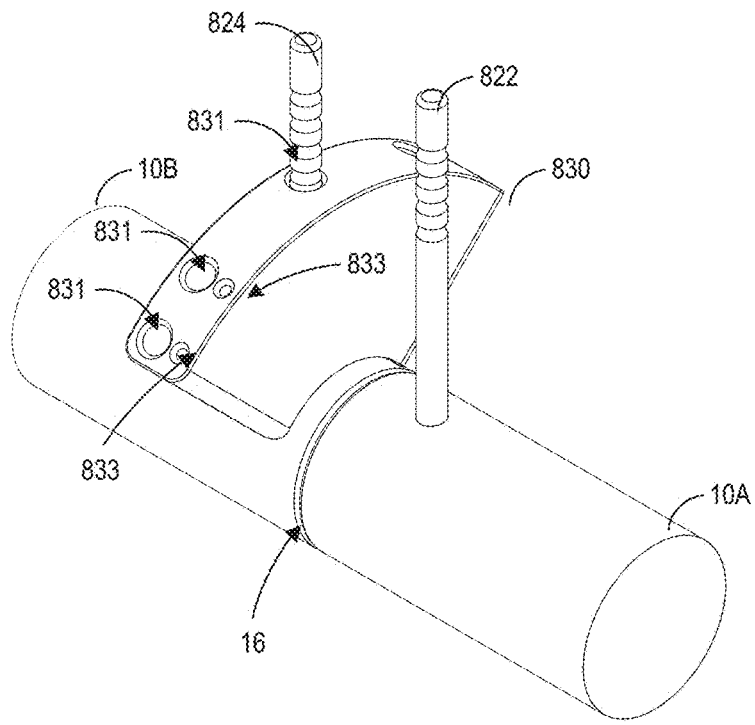

As shown in FIG. 8D, the first drill guide 800 can be removed after the temporary fixation pins 822, 824 have been inserted into the bone portions 10A, 10B respectively. The second drill guide 830 can be placed against the outer surface of the bone portion 10A or 10B, such as the bone portion 10B as shown in FIG. 8D (or the surgical procedure can start with the bone portion 10A). The second drill guide 830 can have a surface to be placed against the outer surface of the bone portions 10A, 10B. The surface can be optionally generally inwardly curved or concave. The second drill guide 830 can have a plurality of first channels 831 (for example, two, three, four, five, six, or more) extending from the optionally concave surface through a height of the second drill guide 830 to an opposite surface of the second drill guide 830. The plurality of the first channels 831 can be substantially aligned and spaced apart (for example, with uniform spacing or varying spacing) along a length of the second drill guide 830. The first channel 831 is sized to fit the temporary fixation pin 822, 824 as the second drill guide 830 is placed against the bone portion 10A, 10B. A user can adjust which first channel 831 is fitted over the temporary fixation pin 822, 824, such as shown in FIG. 8D (using the first channel 831 at or near the center of the second drill guide 830 along the length of the second drill guide 830) and FIG. 8E (using the first channel 831 on one side of the second drill guide 830 along the length of the second drill guide 830).

The second drill guide 830 can include a plurality of second channels 833 (for example, two, three, four, five, six, or more) extending from the optionally concave surface through the height of the second drill guide 830 to the opposite surface of the second drill guide 830. Alternatively, the second pluralities of channels 833 can be replaced by a slot that includes an infinite number of channel positions. The plurality of the second channels 833 can be substantially aligned and spaced apart (for example, with uniform spacing or varying spacing) along the length of second drill guide 830. As shown in FIG. 8D, the plurality of second channels 833 can be along the optionally concave surface such that the plurality of second channels 833 intersect and/or pass the centerline of the arc of the concave surface at a known distance below the bone contacting surface of the second drill guide 830. This configuration ensures that the screws 302, 304 pass the bone engaging legs 152, 154 of the clip 102 prior to reaching the depth of the free end of the bone engaging legs 152, 154 for all combinations of the channels 831 and 833 except in the case when the user selects one of the channels 831 and one of the channels 833 which are directly adjacent to one another across the width of the second drill guide 830. In that case, the screws 302 or 304 is implanted generally parallel to the leg 152 or 154 of the clip. A plane through axes of the plurality of first channels 831 can be generally parallel to a plane through axes of the plurality of second channels 833. The two planes can be adjacent to each other across a width of the second drill guide 830 and be separated such that each of the plurality of first channels 831 is separated from a nearest or adjacent second channel 833 by a fixed distance. The size of the fixed distance can be varied on different drill guides to increase or decrease the contact between the clip 102 and the screws 302, 304 as described above. In some embodiments, a second channel 833 can be located adjacent each first channel 831 across the width of the second drill guide 830. In other embodiments, the number of the first and second channels 831, 833 need not be the same. In some embodiments, the second channels 833 can be staggered with the first channels 831 instead of being adjacent to each other across the width of the second drill guide 830.

Bones can have irregularities on the outer surfaces, which are not illustrated in the schematic representation of bone portions 10A, 10B for simplicity. Using separate drill guides for drilling holes in the bone portions for the screws and the clip respectively can allow each of the first or second drill guide 800, 830 to better follow the contour of the outer surface of the bone portions and be more easily adjusted for irregularities on different parts of the bone surfaces.

Figure 8E:
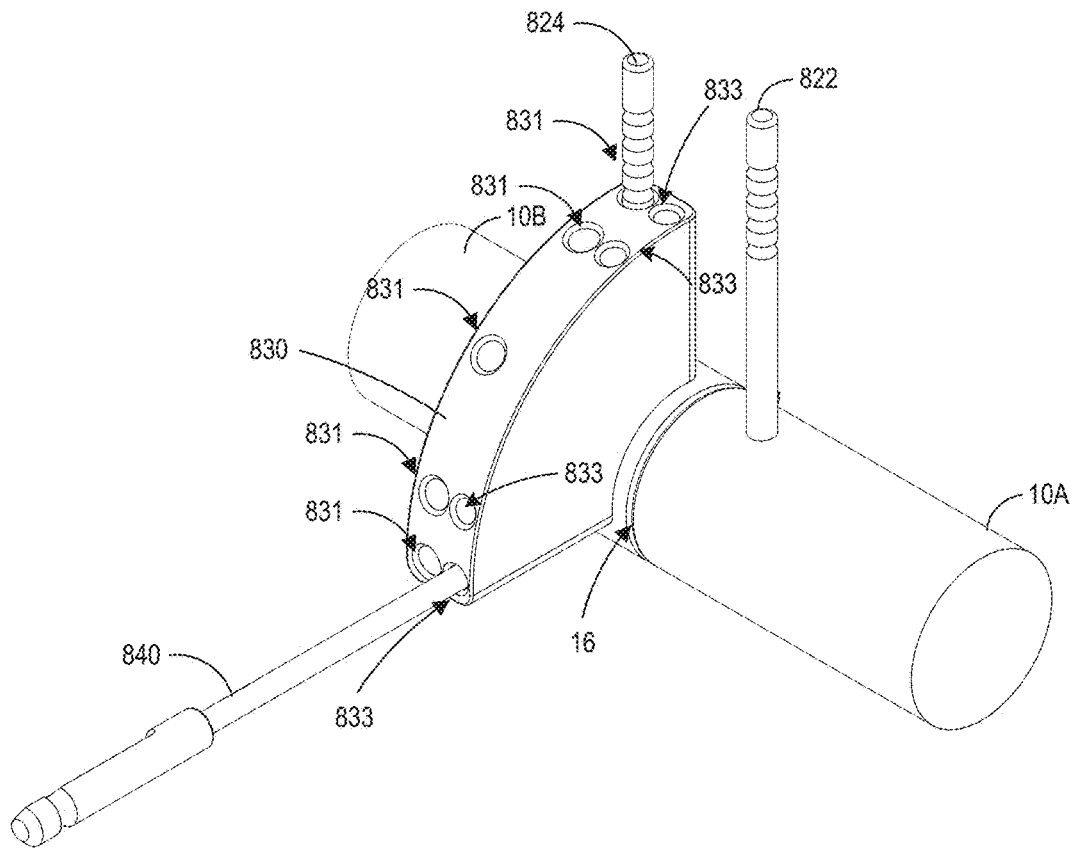

As shown in FIG. 8E, the second channel 833 can be sized to slidably receive a hole creation device 840 (such as a drill bit, bone punch, reamer, broach or other such device), which can be of the same size as the first drill bit 820 or a different size that is either bigger or smaller than the size of the first drill bit 820. The second drill guide 830 can have the height such that the second channel 833 is long enough to guide the second drill bit 840 to travel through cortical regions on generally diametrically opposite sides of the bone portions 10A, 10B. In some embodiments, the second drill bit 840 can drill bores into the bone portions 10A, 10B. In some implementations, such as shown in FIG. 8E, the second drill bit 840 can be inserted into the second channel 833 that is the furthest away from the first channel 831 in which the temporary fixation pin 824 is inserted. In other implementations, a different second channel 833 can be used.

Figure 8F:
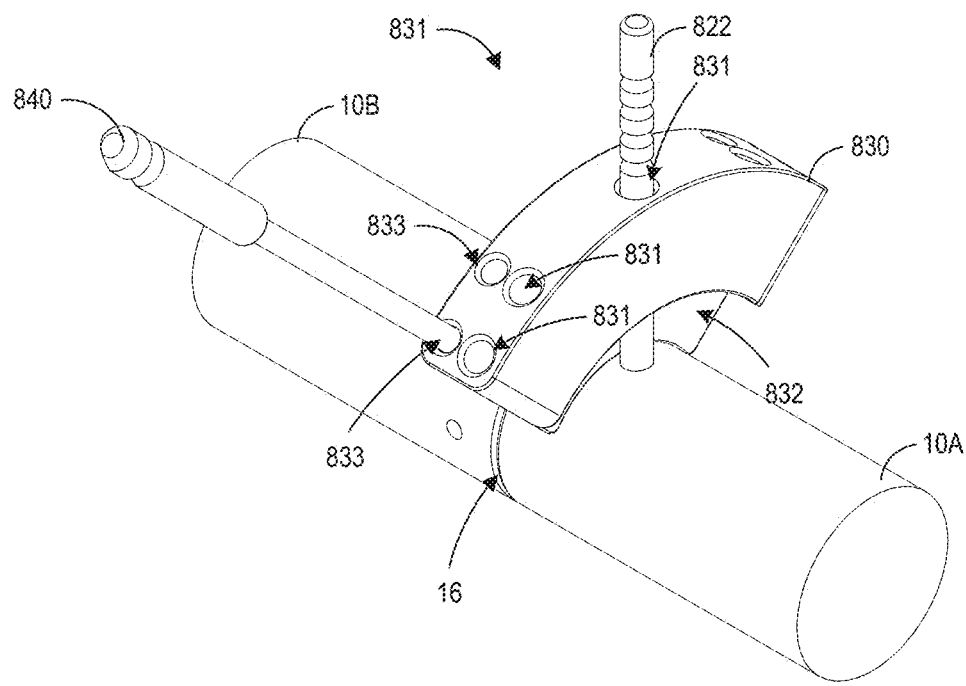
Figure 10B:
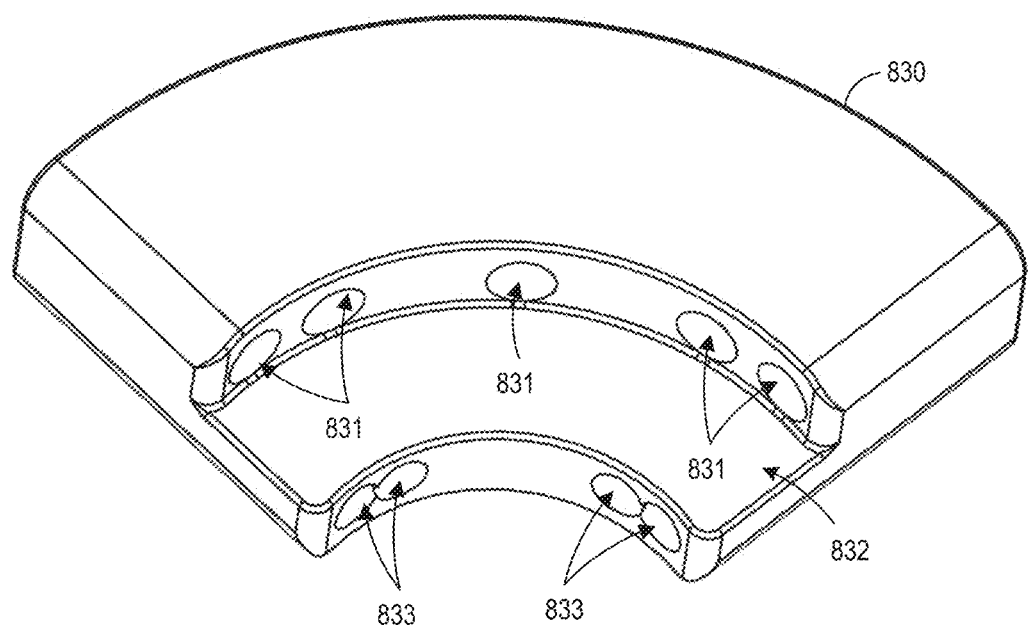
FIG. 10B illustrates a perspective view of an example drill guide for preparing bone portions for the implantation of the screws depicted in FIGS. 3A-6.

As shown in FIG. 8F, the temporary fixation pin 824 and the second drill bit 840 can be removed from the bone portion 10B after the desired holes have been drilled. The second drill guide 830 can be rotated 180° about its radial axis to couple with the inserted temporary fixation pin 822 to provide guidance for drilling a hole on the opposite side of the discontinuity 16 in the bone portion 10A. When in use, the second drill guide 830 can be oriented such that each of the second channels 833 is closer to the discontinuity 16 than the nearest first channels 831. As shown in FIGS. 8F and 10B, the second drill guide 830 can include an undercut portion 832 in the side where the first channels 831 are located, making that side shorter than the side in which the second channels 833 are located. The undercut portion 832 can allow a better visual confirmation of the position of the temporary fixation pin 832, 834 when a hole is drilled in the bone portion 10A, 10B via one of the second channels 833. As shown in FIG. 8F, the second drill bit 840 can be used to drill a hole in the bone portion 10B via a second channel 833 closer to the first channel 831 in which the temporary fixation pin 822 is inserted than the spacing between the first channel 831 and the second channel 833 used to create the hole in the bone portion 10B as shown in FIG. 8E.

Figure 8G:
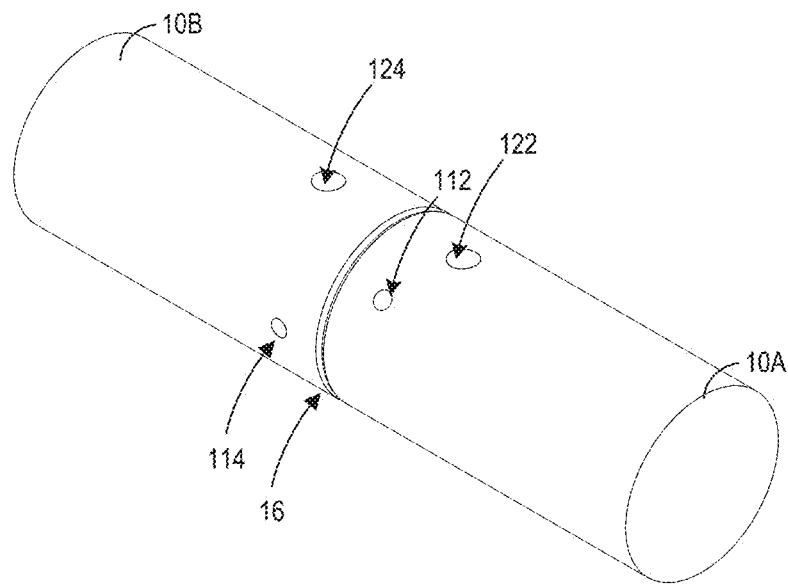

As shown in FIG. 8G, the temporary fixation pin 822 and the second drill bit 804 can be removed from the bone portion 10A after the desired holes have been drilled. The bone portion 10A can have a first hole 122 formed by the first drill bit 820 and a second hole 112 formed by the second drill bit 840. The bone portion 10B can have a first hole 124 formed by the first drill bit 820 and a second hole 114 formed by the second drill bit 840. The first hole 122 is at a first angle with the second hole 112. The first hole 124 is at a second angle with the second hole 114. The first and second angles are different in some implementations, such as shown in FIG. 8G. The first hoes 112, 122 and the second holes 114, 124 can also be coplanar (that is, the first and/or second angles can be 0 degree).

Figure 8H:
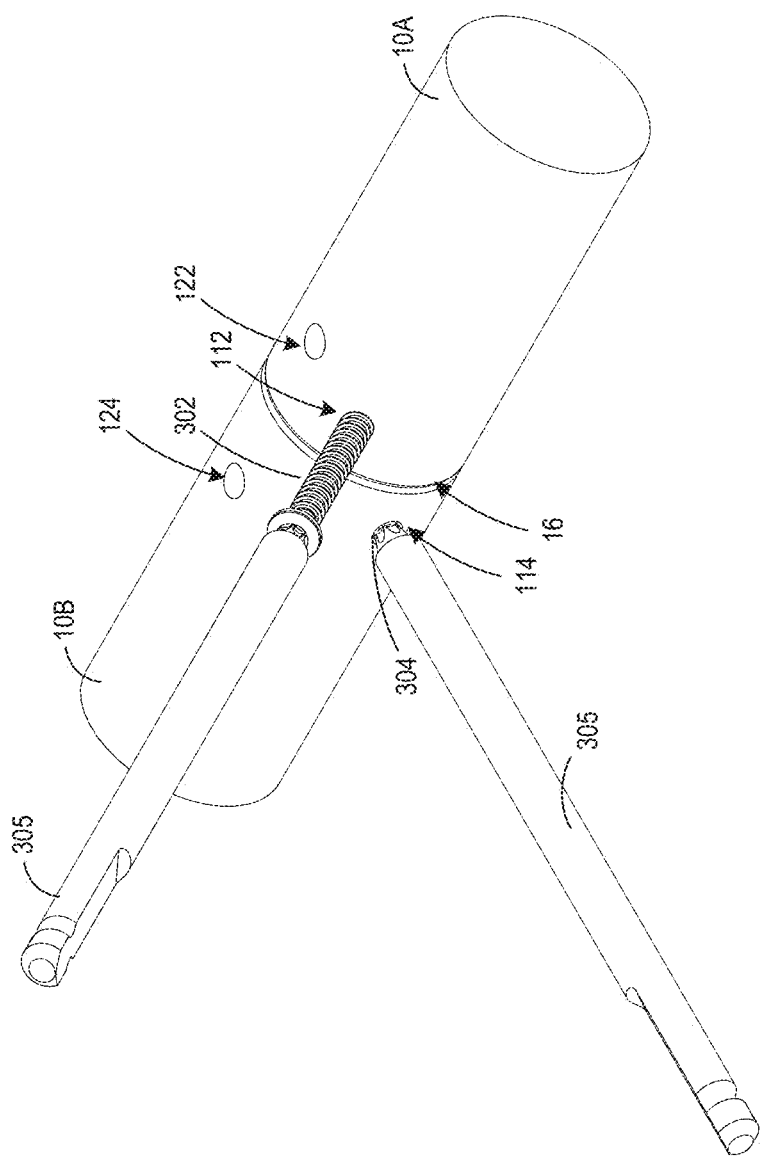

As shown in FIG. 8H, the second holes 112, 114 can be sized to threadedly receive the screws 302, 304 respectively. The screws 302, 304 can be implanted using a screwdriver 305. Although a screwdriver 305 is illustrated for each screw 302, 304, which may deliver the screws 302, 304 simultaneously or sequentially, in some implementations, a single screwdriver 305 can be used to deliver the screws 302, 304 sequentially in any order.

Figure 8I:
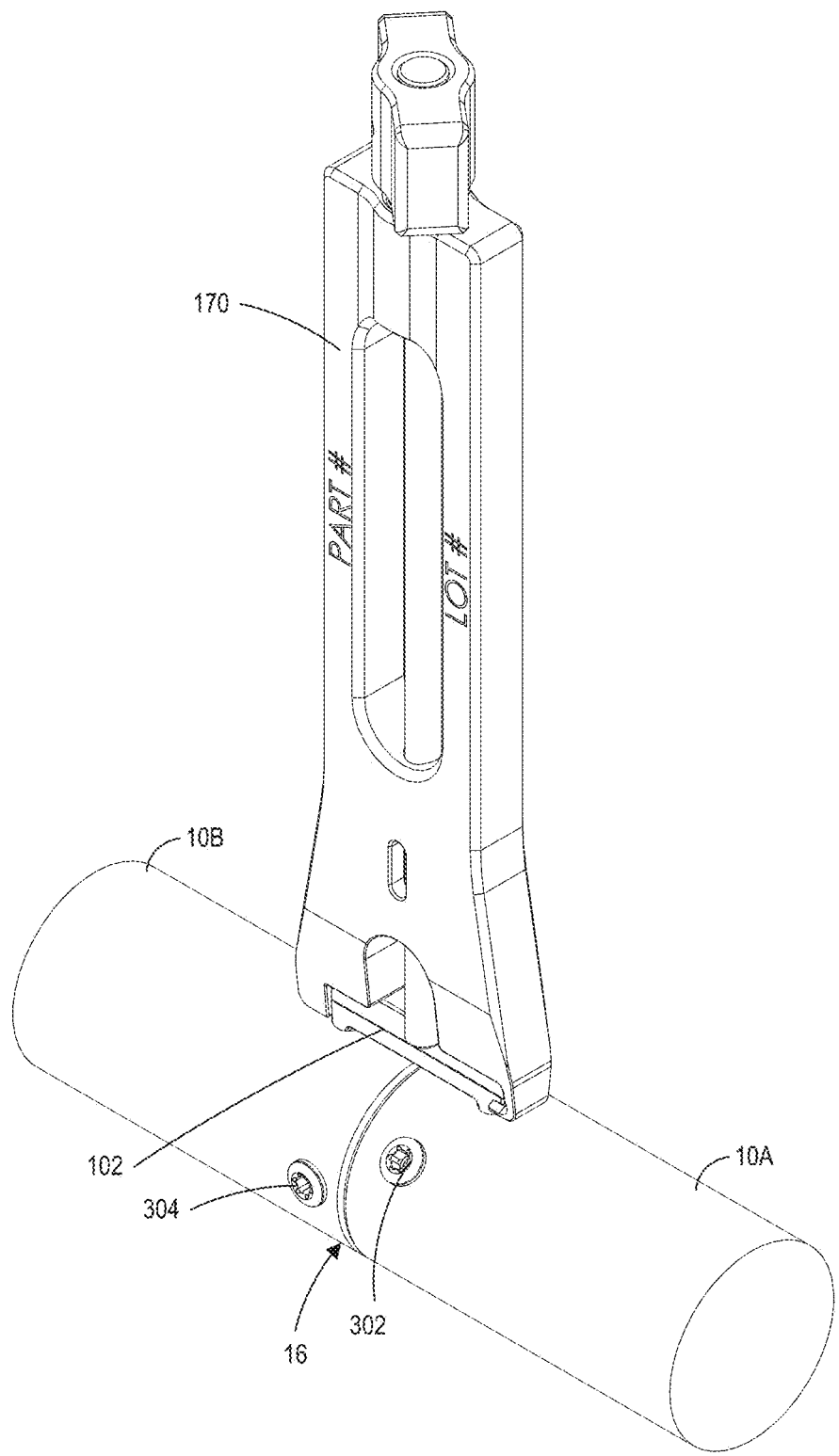

In some implementations, such as shown in FIG. 8I, after the screws 302, 304 have been delivered, the clip 102 in the deformed configuration can be delivered using the inserter tool 170. The first holes 122, 124 can be sized so that the bone engaging legs 152, 154 (hidden in this view) of the clip 102 can frictionally fit into the first holes 122, 124. The inserter tool 170 can be removed after substantially the entire length of the bone engaging legs 152, 154 is embedded into the bone portions 10A, 10B. Removing the inserter tool 170 allows the legs 152, 154 to compress towards each other as the clip 102 relaxes towards its free configuration, thereby creating compression across the discontinuity 16. As the legs 152, 154 begin to converge, the legs 152, 154 may contact the screws 302, 304 to distribute the compressive load.

Figure 9A:
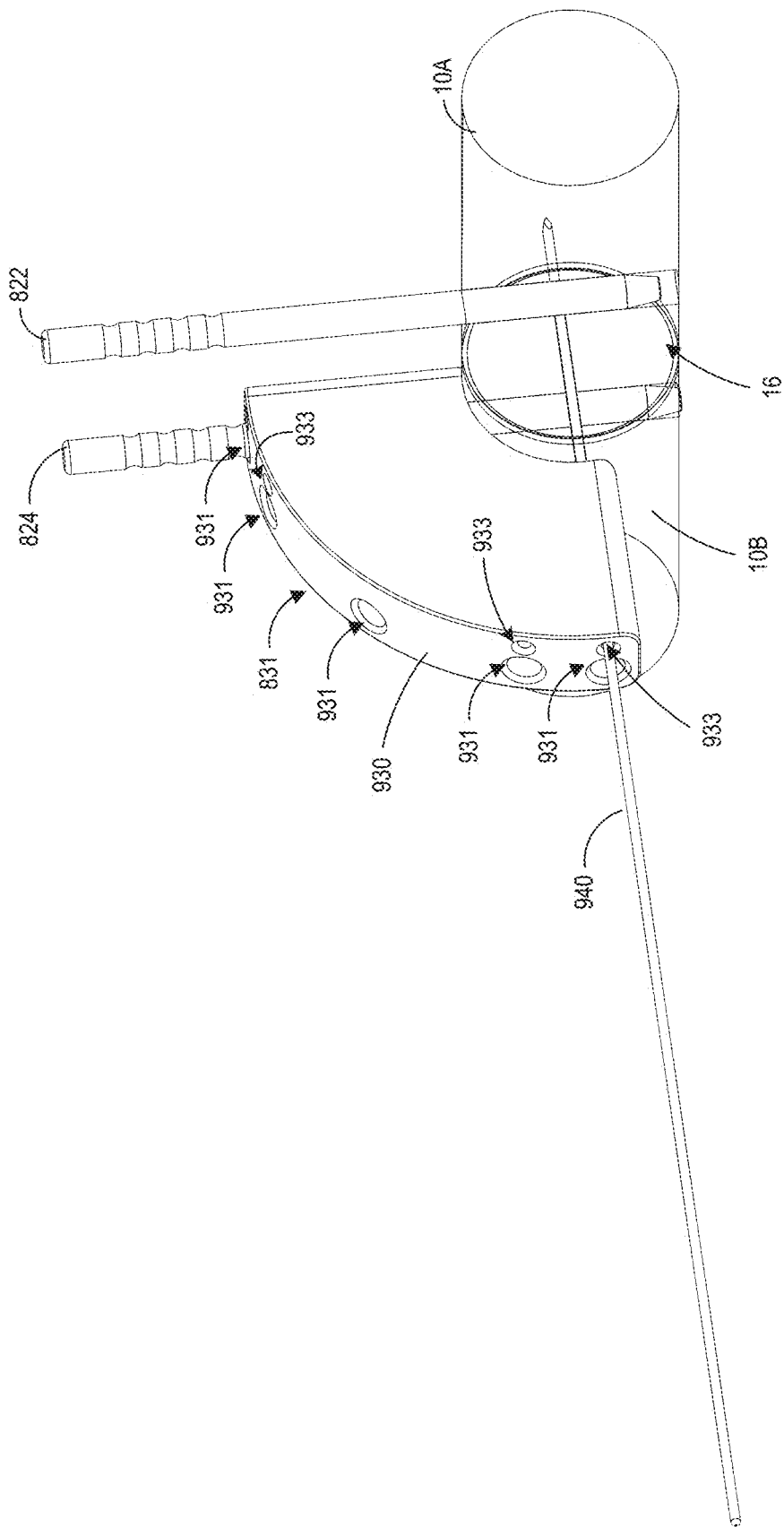
FIGS. 9A-9D illustrate certain steps for implanting the fixation system of FIGS. 4A-5C.

As shown in FIGS. 9A-9E, a method of fixing bone portions across the discontinuity 16 using the fixation system 400 as shown in FIGS. 4A-4B can include one or more of the following steps. A person of ordinary skill will appreciate from the disclosure herein that some steps described with reference to and shown in FIGS. 8A-8I, for example, FIGS. 8A-8C, apply to the method of delivering the fixation system 400, although those steps are not shown or described again in the description of delivering the fixation system 400 for brevity. After the first drill guide 800 and the first drill bit 820 have been used to drill holes (through or blind) in the bone portions 10A, 10B on opposite sides of the discontinuity 16 for receiving the temporary fixation pins 822, 824, such as shown in FIG. 9A, a second wire guide 930 can be placed against the outer surface of the bone portion 10A or 10B, such as the bone portion 10B as shown in FIG. 9A (in other embodiments, the surgical procedure can start with the bone portion 10A). The second wire guide 930 can have any of the features of the second drill guide 830, except that the diameter of the second channels 933 are smaller than the diameter of the second channels 833 of the second drill guide 830. The same or similar features in the second drill guide 830 and second wire guide 930 share the same last two digits. Therefore, not all the features of the second wire guide 930 are described for brevity. The second channels 933 can be sized to slidably fit a k-wire 940. In some implementations, such as shown in FIG. 9A, the k-wire 940 can be inserted into the second channel 933 that is the furthest away from the first channel 931 in which the temporary fixation pin 824 is inserted across the length of the second wire guide 930.

Figure 9B:
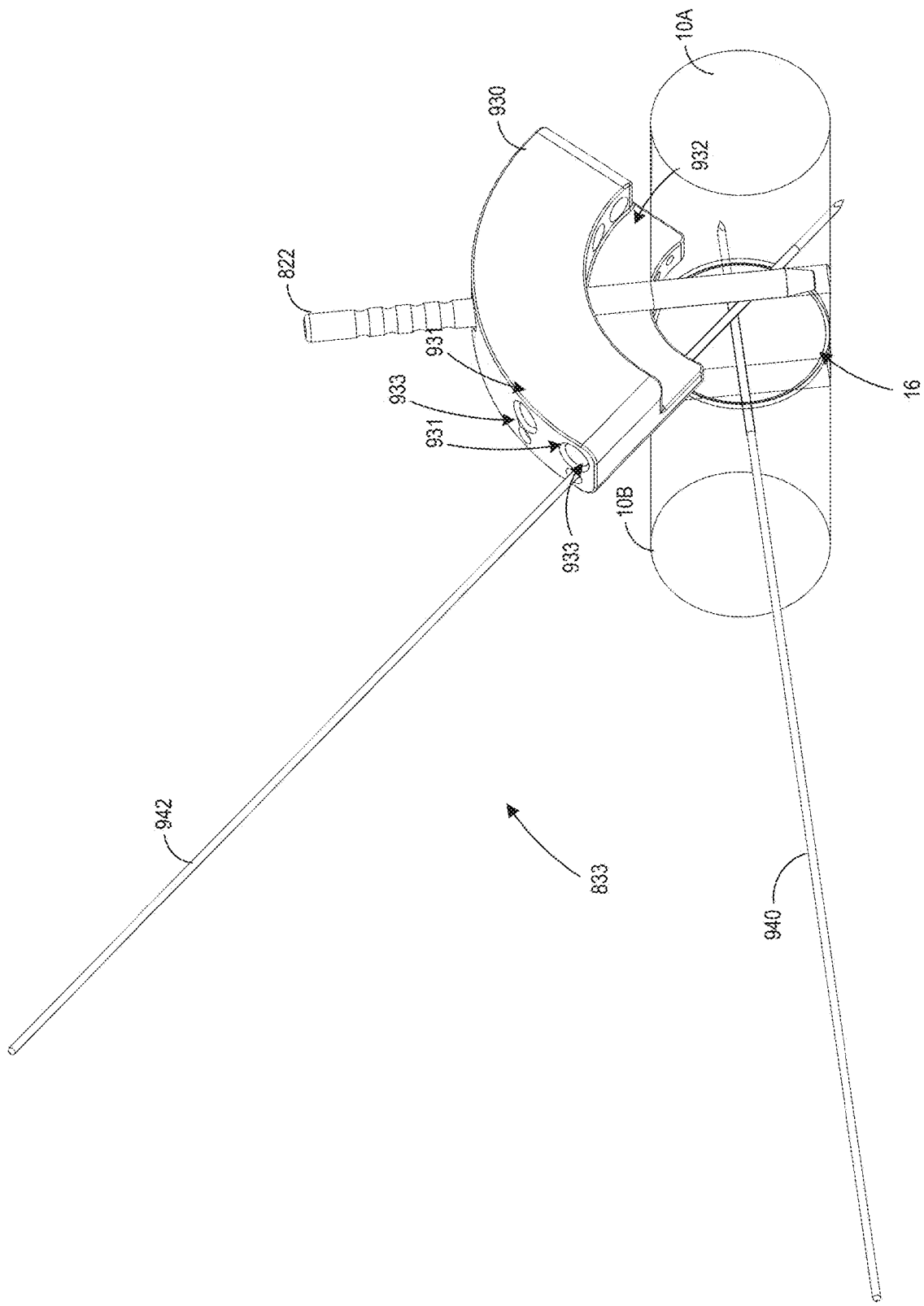

As shown in FIG. 9B, the temporary fixation pin 824 can be removed from the bone portion 10B, with the k-wire 940 left in the bone portion 10B. The second wire guide 930 can be rotated 180° about its radial axis to couple with the inserted temporary fixation pin 822 to provide guidance for inserting a second k-wire 942 on the opposite side of the discontinuity 16 in the bone portion 10A. When in use, the second wire guide 930 can be oriented such that each of the second channels 933 are closer to the discontinuity than the nearest first channels 931. The second wire guide 930 can include an undercut portion 932 in the side where the first channels 931 are located, making that side shorter than the side in which the second channels 933 are located. The undercut 932 can allow a better visual confirmation of the position of the temporary fixation pin 822, 824 when a hole is drilled in the bone portion 10A, 10B via one of the second channels 933. A second k-wire 942 can be inserted (for example, by being impacted using a mallet or otherwise) in the bone portion 10B via a second channel 933. The circumferential spacing between the second channel 933 receiving the second k-wire 942 and the temporary fixation pin 822 can be selected to be smaller than the circumferential spacing between the first k-wire 940 and the and temporary fixation pin 824 as shown in FIG. 9A so that the angle between the second k-wire 942 and the temporary fixation pin 822 can be smaller between the angle between the first k-wire 940 and the temporary fixation pin 824 as shown in FIG. 9A.

Figure 9C:
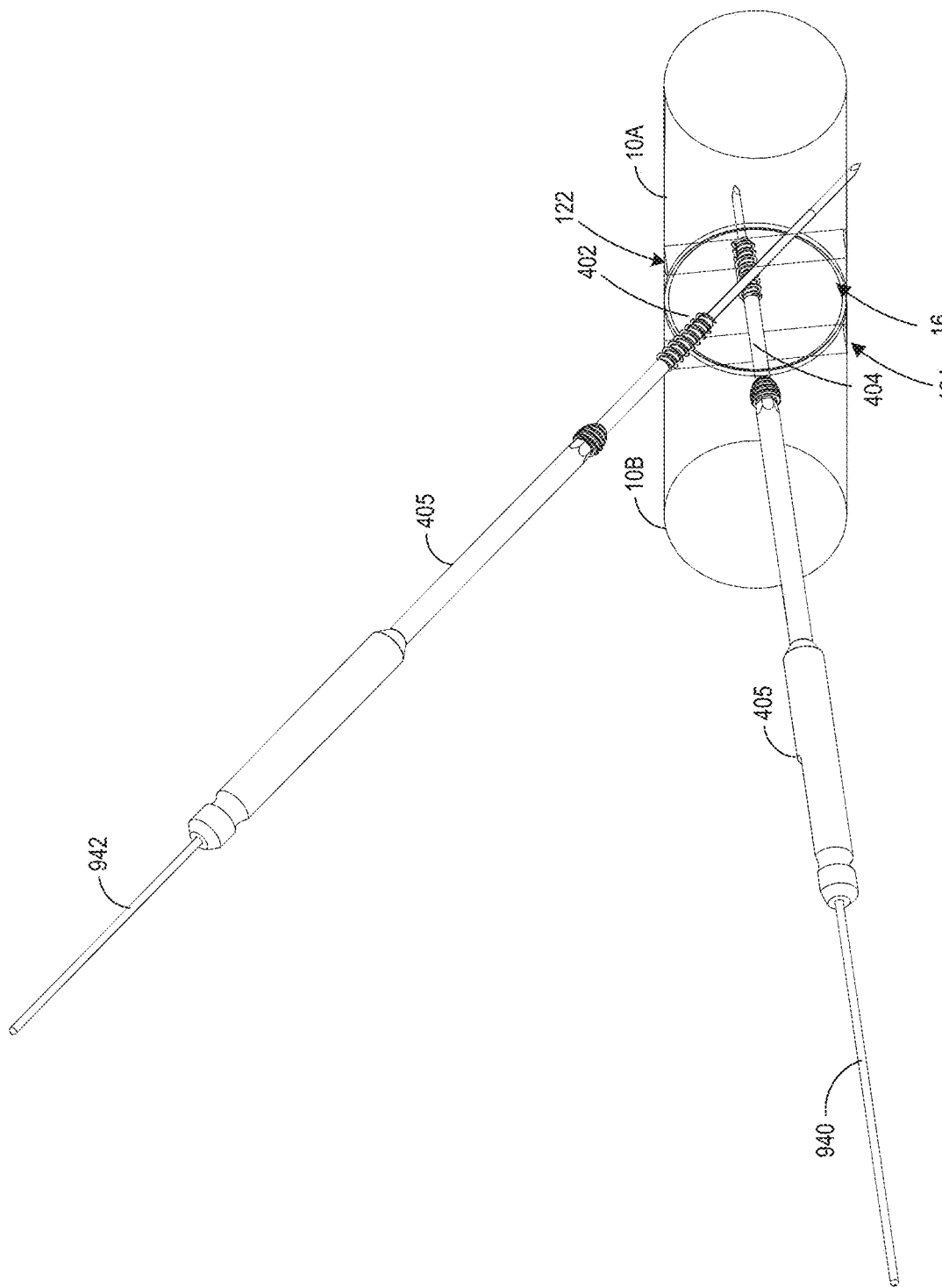

As shown in FIG. 9C, the temporary fixation pin 822 can be removed from the bone portion 10A, with the k-wires 940, 942 left in the bone portions 10B, 10A respectively. The bone portion 10A can have a first hole 122 holes (through or blind) formed by the first drill bit 820. The bone portion 10B can have a second hole 124 holes (through or blind) formed by the first drill bit 820. The first hole 122 is at a first angle with the second k-wire 942. The second hole 124 is at a second angle with the K-wire 940. The first and second angles are different in some implementations such as shown in FIG. 9C. The cannulated screws 402, 404 can be slid over the k-wires 940, 942 and implanted using a cannulated screwdriver 405. Although a screwdriver 405 is illustrated for each screw 402, 404, which may deliver the screws 402, 404 simultaneously or sequentially, in other embodiments, a single cannulated screwdriver 405 can be used to deliver the screws 402, 404 sequentially in any order. After the screws 402, 404 have been implanted, the k-wires 940, 942 may be removed.

Figure 9D:
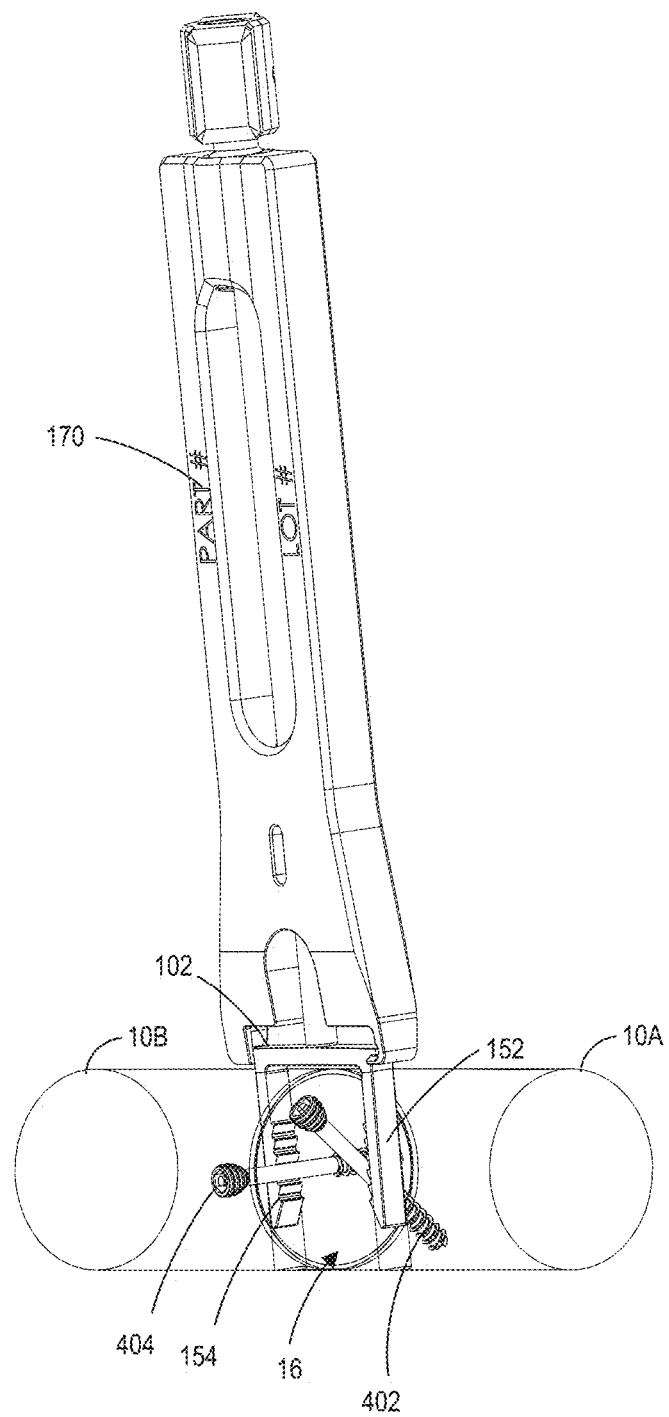

In some implementations, such as shown in FIG. 9D, after the screws 402, 404 have been delivered, the clip 102 in the deformed configuration can be delivered using the inserter tool 170. The first holes 122, 124 can be sized so that the bone engaging legs 152, 154 (hidden in this view) of the clip 102 can fit into the first holes 122, 124. The inserter tool 170 can be removed after substantially the entire length of the bone engaging legs 152, 154 is embedded into the bone portions 10A, 10B. Removing the inserter tool 170 allows the legs 152, 154 to compress towards each other as the clip 102 relaxes towards its free configuration, thereby creating compression across the discontinuity 16. As the legs 152, 154 begin to converge, the legs 152, 154 may contact the screws 402, 404 to distribute the compressive load.

As shown in FIGS. 11A-11E, a method of fixing bone portions across the discontinuity 16 using the fixation system 400 as shown in FIGS. 3A-5C can include one or more of the following steps. A person of ordinary skill will appreciate from the disclosure herein that some steps described with reference to and shown in FIGS. 8A-8I and 9A-9D may apply to the method of delivering the fixation system 400, although those steps are not shown or described again for brevity with reference to FIGS. 11A-11E.

A third drill guide 1100 such as shown in FIGS. 11A-11C can replace the first drill guide 800 and the second drill guide 830 or second wire guide 930. The third drill guide 1100 can be used to drill holes configured for the legs 152, 154 of the clip 102, such as shown in FIG. 11B, and to insert k-wires 940, 942 after the temporary fixation pins 822, 824 have temporarily coupled the third drill guide 1100 to both of the bone portions 10A, 10B, such as shown in FIG. 11C. The third drill guide 1100 can combine features of the first drill guide 800 and the second wire guide 930 (or second drill guide 830 if non-cannulated screws 302, 304 are used) described herein. Features of the first, second, and third guides 820, 830, 930, 1100 share the same last two digits. Therefore, not the all the features of the third drill guide 1100 are described for brevity. The third drill guide 1100 can advantageously simplify the surgical procedure and/or reduce surgical time as the same instrument is used for drilling all the holes in the bone portions 10A, 10B.

The third drill guide 1100 can include a pair of first channels 1131, which can be sized for guiding the first drill bit 820 to drill a hole in the bone portions 10A, 10B for receiving the temporary fixation pins 822, 824. The drill guide 1100 can include a first plurality of (for example, three or more) of second channels 1133 and a second plurality of (for example, three or more) of second channels 1133. Alternatively, the second pluralities of channels 1133 can be replaced by a slot that includes an infinite number of channel positions. Each plurality of second channels 1133 can be aligned or substantially aligned. The first and second pluralities of second channels 1133 can be separated by a gap. The first and second pluralities of second channels 1133 can be located in two generally parallel tabs 1136 respectively. The spacing of the second channels on the two tabs 1136 can be the same or different. The two tabs 1136 can be offset relative to the first channels 1131 such that second channels 1133 are closer to the discontinuity 16 than the first channels 1131. In some embodiments, such as shown in FIGS. 11A-11C, the first and second pluralities of second channels 1133 can be aligned in pairs. When in use, the first channels 1131 and the second channels 1133 can be placed generally symmetrically about the discontinuity 16, such as shown in FIGS. 11A-11C. The k-wires 940, 942 can be inserted into the second channels 1133 that are on opposite sides of the discontinuity 16 so that the k-wires 940, 942 are parallel (such as shown in FIG. 11C) or at an angle to each other (such as shown in FIG. 9B). In an alternative embodiment, the second channels 1133 are used as guides to drill holes for non-cannulated screws to create the fixation system 300 shown in FIGS. 3A and 3B.

Figure 11D:
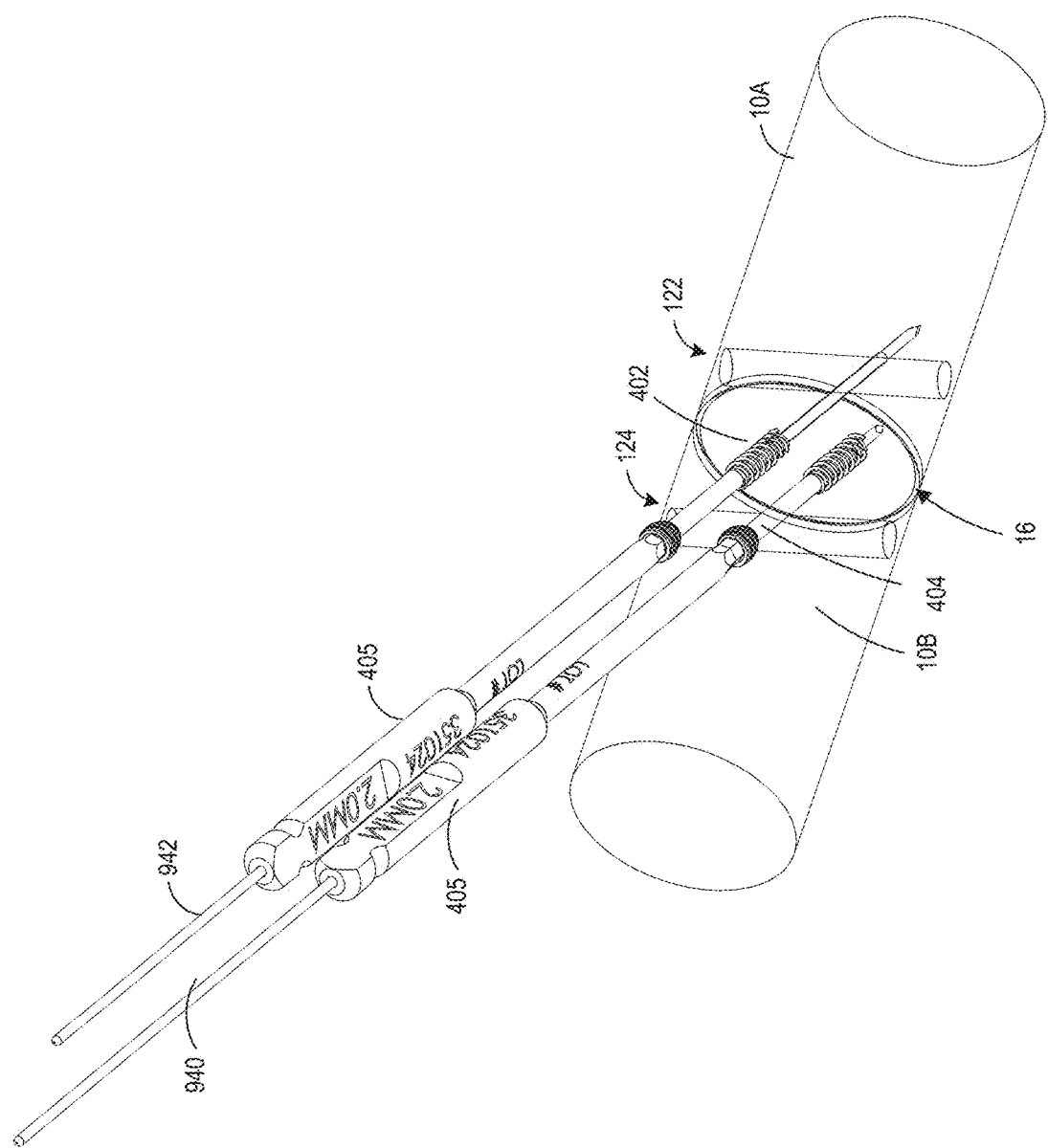

As shown in FIG. 11D, the temporary fixation pins 822, 824 and the third drill guide 1100 can be removed from the bone portions 10A, 10B, with the k-wires 940, 942 left in the bone portions 10B, 10A respectively. The bone portion 10A can have a first hole 122 formed by the first drill bit 820. The bone portion 10B can have a second hole 124 formed by the first drill bit 820. The first hole 122 is at the same angle with the k-wire 942 as the angle between the second hole 124 and the K-wire 940. The angle can also be different if the user chooses a different second channel 1133 or if the second channel 1133 is replaced by a slot as described above. The cannulated screws 402, 404 can be slid over the k-wires 940, 942 and implanted using a cannulated screwdriver 405. Although a screwdriver 405 is illustrated for each screw 402, 404, which may deliver the screws 402, 404 simultaneously or sequentially, in other embodiments, a single cannulated screwdriver 405 can be used to deliver the screws 402, 404 sequentially in any order. After the screws 402, 404 have been implanted, the k-wires 940, 942 may be removed.

Figure 11E:
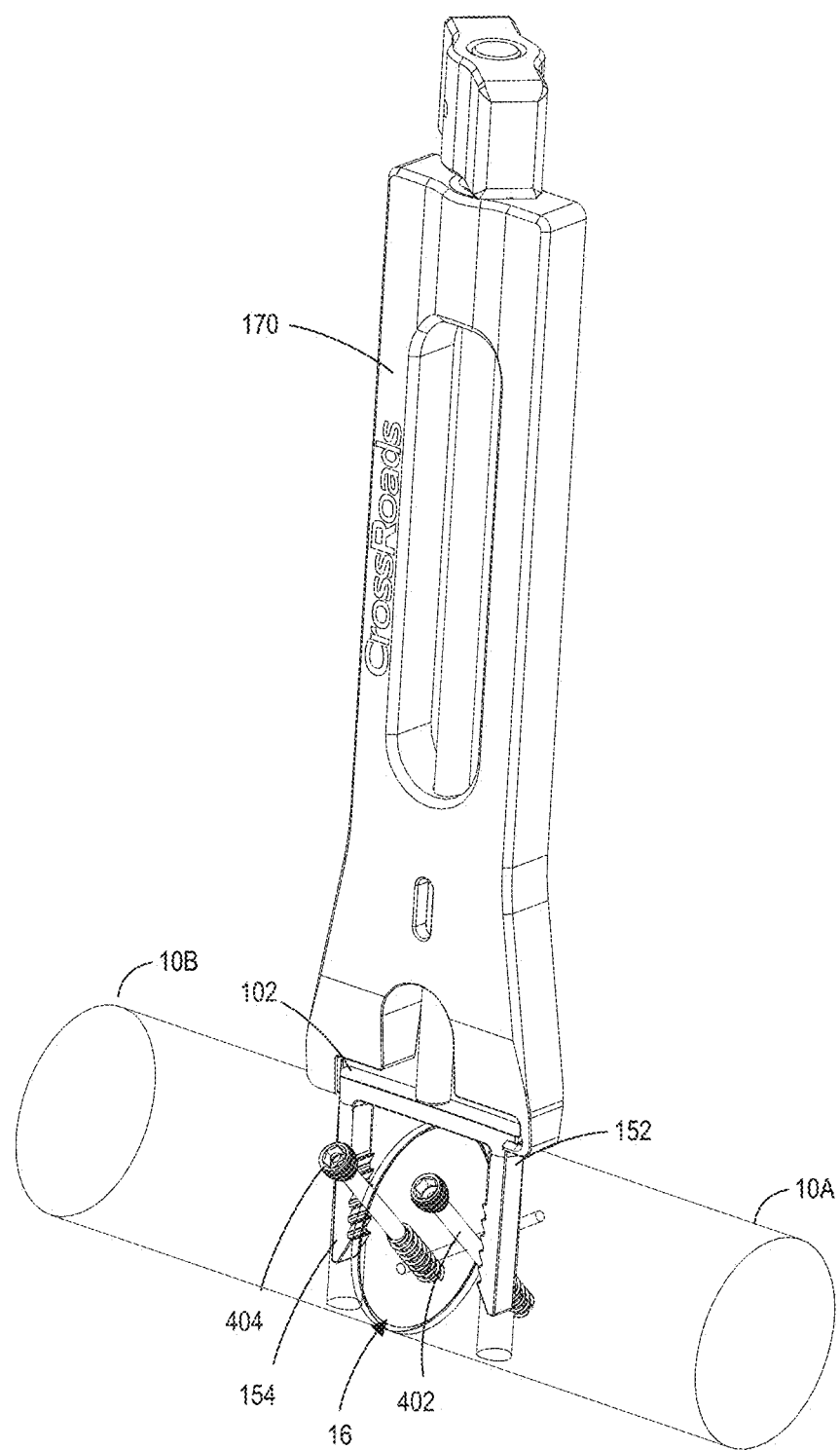

In some implementations, such as shown in FIG. 11E, after the screws 402, 404 have been delivered, the clip 102 in the deformed configuration can be delivered using the inserter tool 170. The first holes 122, 124 can be sized so that the bone engaging legs 152, 154 (hidden in this view) of the clip 102 can frictionally fit into the first holes 122, 124. The inserter tool 170 can be removed after substantially the entire length of the bone engaging legs 152, 154 is embedded into the bone portions 10A, 10B. Removing the inserter tool 170 allows the legs 152, 154 to compress towards each other as the clip 102 relaxes towards its free configuration, thereby creating compression across the discontinuity 16. As the legs 152, 154 begin to converge, the legs 152, 154 may contact the screws 402, 404 to distribute the compressive load.

As shown in FIGS. 12A-12K, another example method of fixing bone portions across the discontinuity 16 using the fixation system 400 as shown in FIGS. 3A-5C can include one or more of the following steps. A person of ordinary skill will appreciate from the disclosure herein that some steps described with reference to and shown in FIGS. 8A-8I, 9A-9D, and 11A-11E may apply to the method of delivering the fixation system 400, although those steps are not shown or described again for brevity with reference to FIGS. 12A-12K.

A fourth drill guide 1200 such as shown in FIGS. 12A-12F can replace the first drill guide 800 and the second drill guide 830 or second wire guide 930, or to replace the third drill guide 1100. The fourth drill guide 1200 can have any of the features of the third drill guide 1110, with the differences described with reference to FIGS. 12A-12F. Features of the first, second, third, and fourth guides 800, 830, 930, 1100, 1200 share the same last two digits. Therefore, not the all the features of the third drill guide 1200 are described for brevity.

The fourth drill guide 1200 can include a pair of first channels 1231, which can be sized for guiding the first drill bit 820 to drill a hole in the bone portions 10A, 10B for receiving the temporary fixation pins 822, 824. The fourth drill guide 1200 can include a first tab 1236 and a second tab 1236 extending respectively from the two first channels 1231. The first and second tabs 1236 can be generally parallel to each other. Each tab 1236 can include a second channel 1233. Each second channel 1233 can include an open slot 1235 (more clearly shown in, e.g., FIG. 12C) extending along a longitudinal axis of the second channel 1233. The open slot 1235 can have a width that is at least greater than an outer diameter of the k-wires 940, 942. The two tabs 1136 can be offset relative to the first channels 1231 such that the second channels 1233 are closer to the discontinuity 16 than the first channels 1231.

Figure 12A:
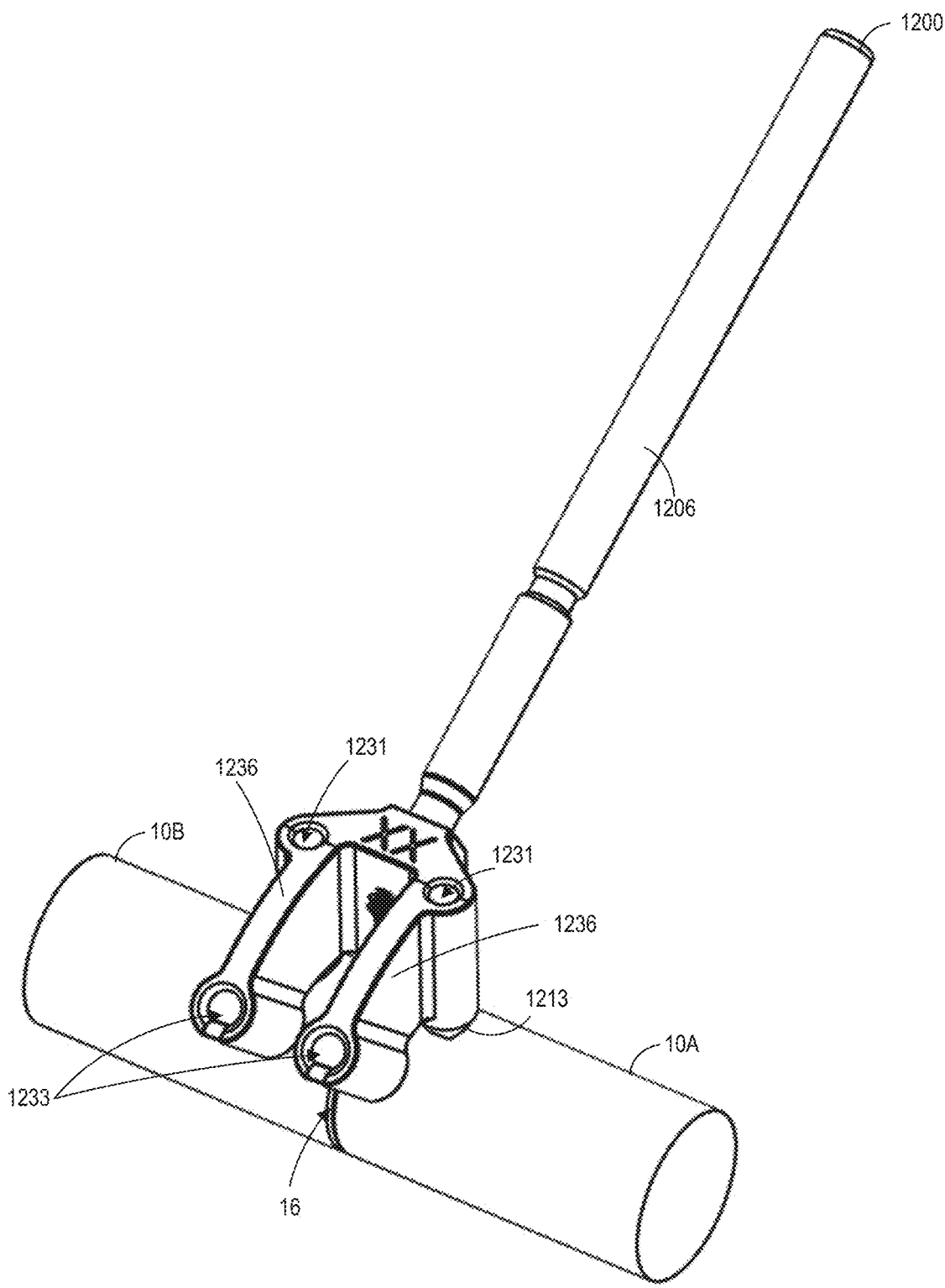
FIGS. 12A-12K illustrate certain steps using another alternative drill guide for implanting the fixation system of FIGS. 3A-5C.
Figure 12B:
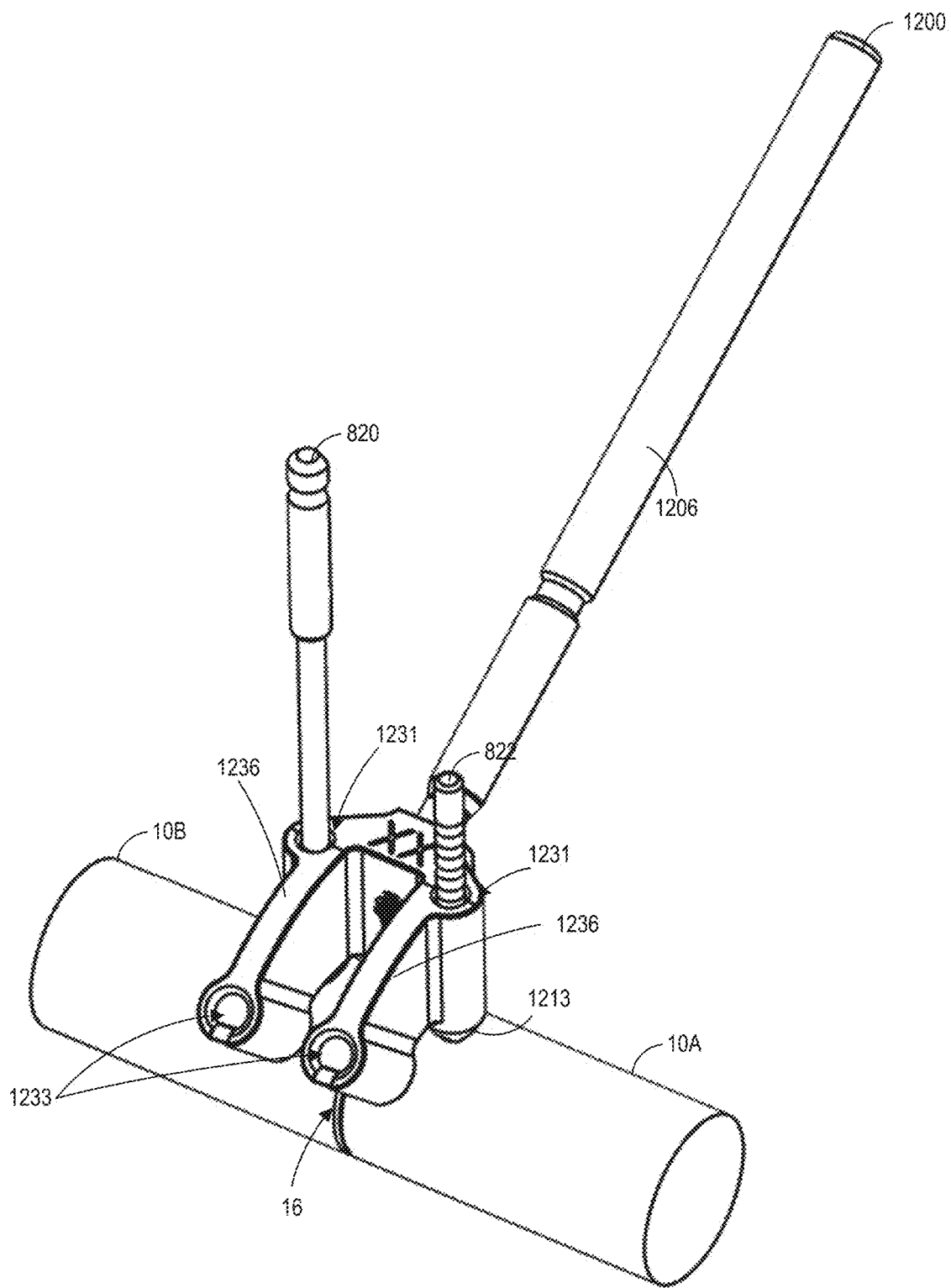

As shown in FIG. 12A, a bone-contacting end of the fourth drill guide 1200 (which includes the first channels 1231) can terminate in a plurality of tips 1213 rather than a continuous ring. When in use, the first channels 1231 and the second channels 1233 can be placed generally symmetrically about the discontinuity 16. As shown in FIG. 12B, the fourth drill guide 1200 can be used to drill holes configured for the legs 152, 154 of the clip 102 via the first channels 1231. The temporary fixation pins 822, 824 can be placed in the holes drilled by the first drill bit 822, 824 (not shown in FIG. 12B) guided by the first channels 1231.

Figure 12C:
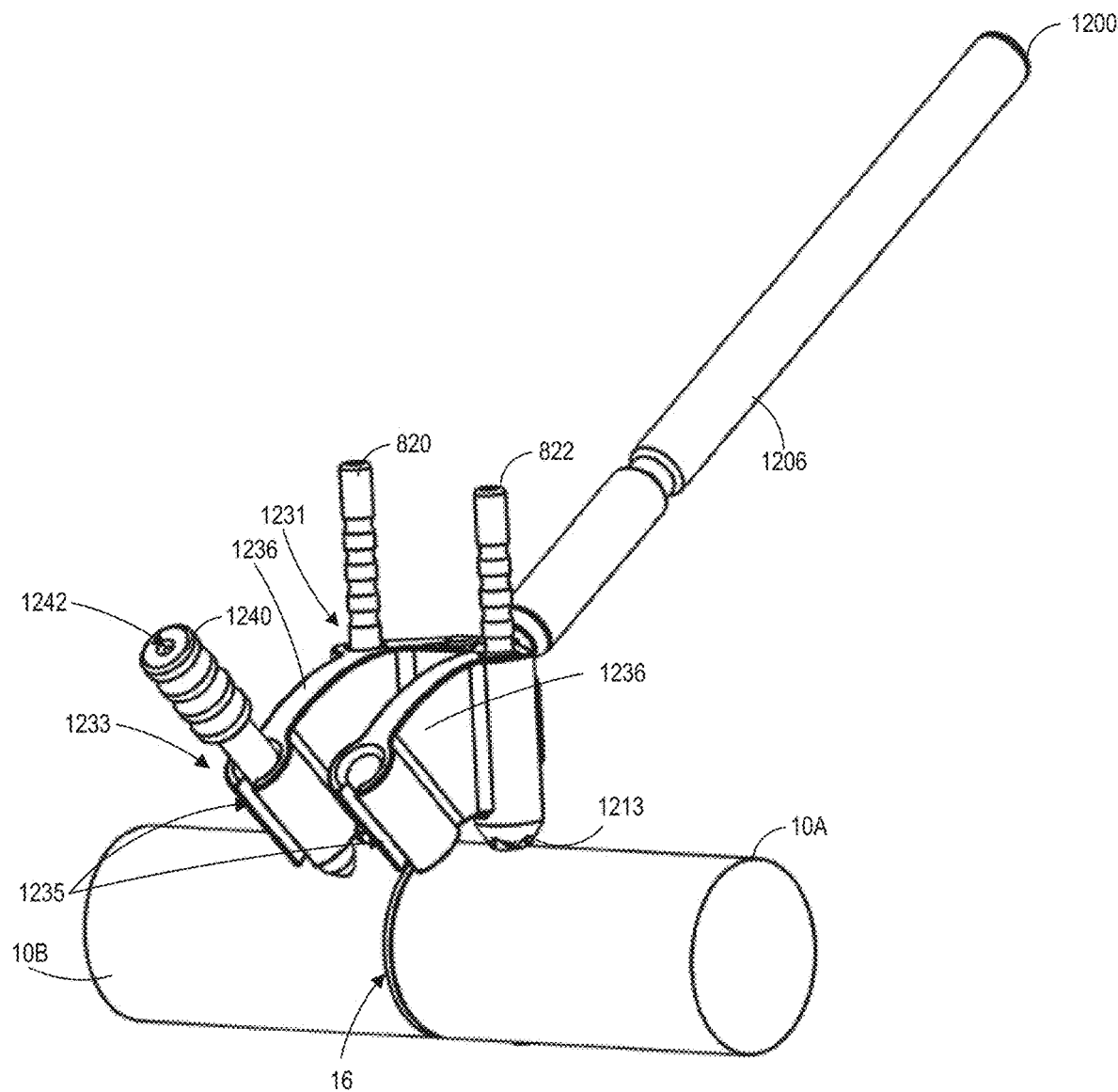
Figure 12D:
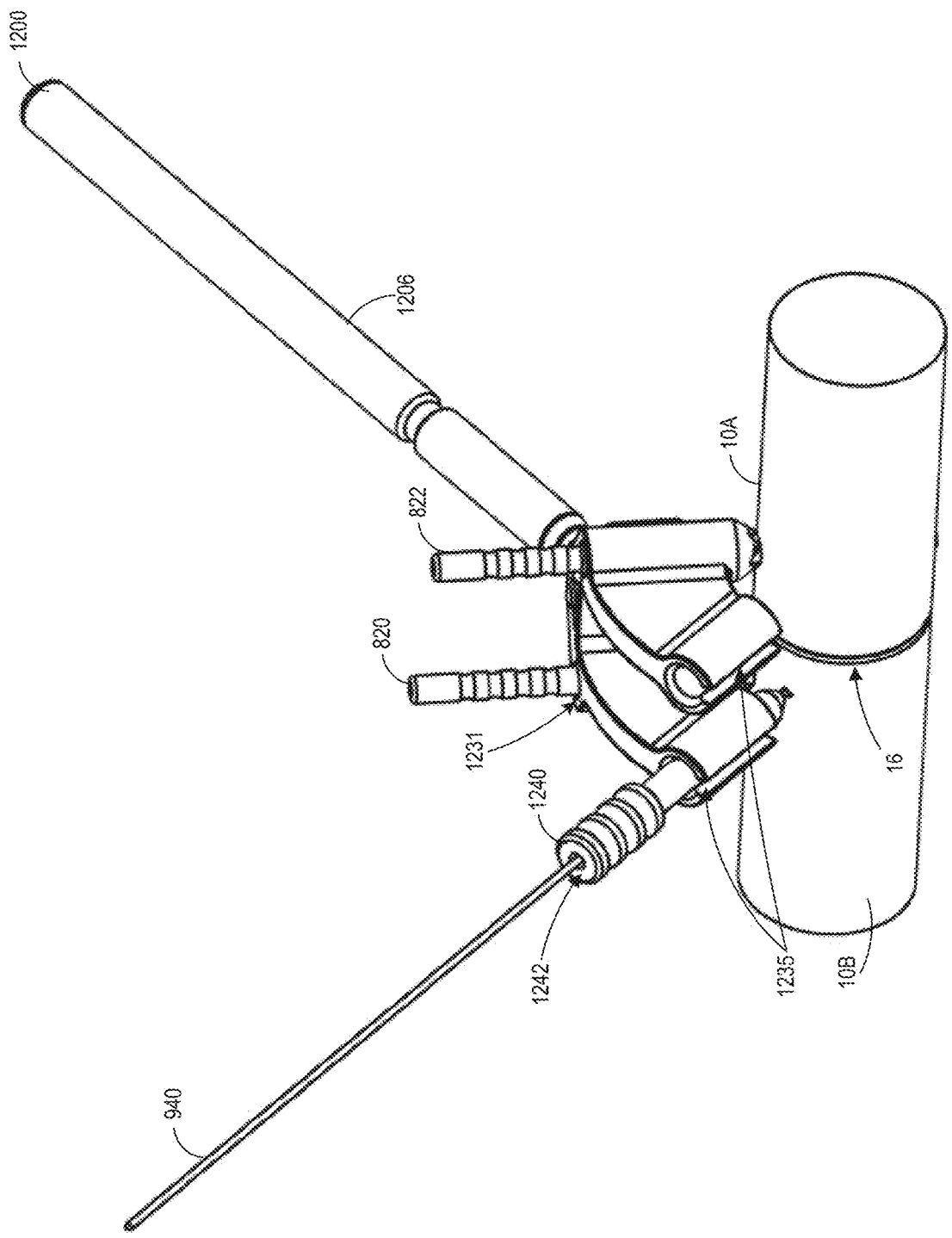
Figure 12E:
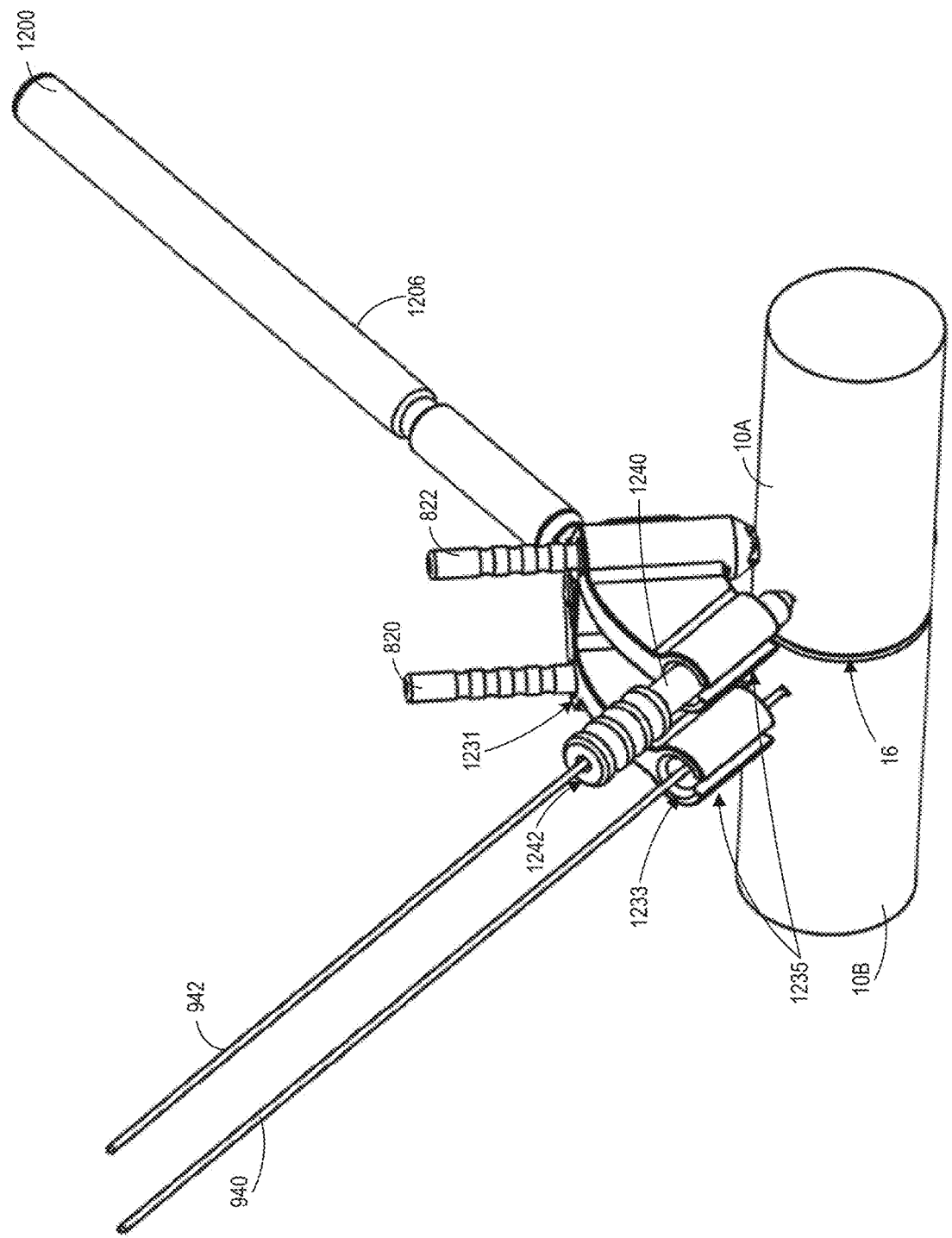

As shown in FIGS. 12C-12E, a guide tube 1240 can be used to guide the insertion of the k-wires 940, 942 via the second channels 1233 into the bone portions 10A, 10B. The guide tube 1240 can allow the bearing surface of the k-wire 940, 942 to be docked directly to the surface of the bone portion 10B, 10A to help prevent skiving of the k-wire 940, 942. The fourth drill guide 1200 and the guide tubes 1240 can be used to insert the k-wires 940, 942 after the temporary fixation pins 822, 824 have temporarily coupled the fourth drill guide 1200 to both of the bone portions 10A, 10B.

As shown in FIG. 12C, the guide tube 1240 can be inserted into one of the second channels 1233. The guide tube 1240 can include a post with an outer diameter sized to be slidably received by the second channel 1233. The guide tube 1240 can include a cannulation 1242 sized to slidably receive one of the k-wires 940, 942. In some embodiments, the guide tube 1240 can include a ribbed portion configured for easier manipulation by hand for sliding into and/or away from the second channel 1233. As shown in FIG. 12D, the k-wire 940 can be inserted into the cannulation 1242 of the guide tube 1240. The k-wires 940 can be driven into the bone portion 10B.

Figure 12F:
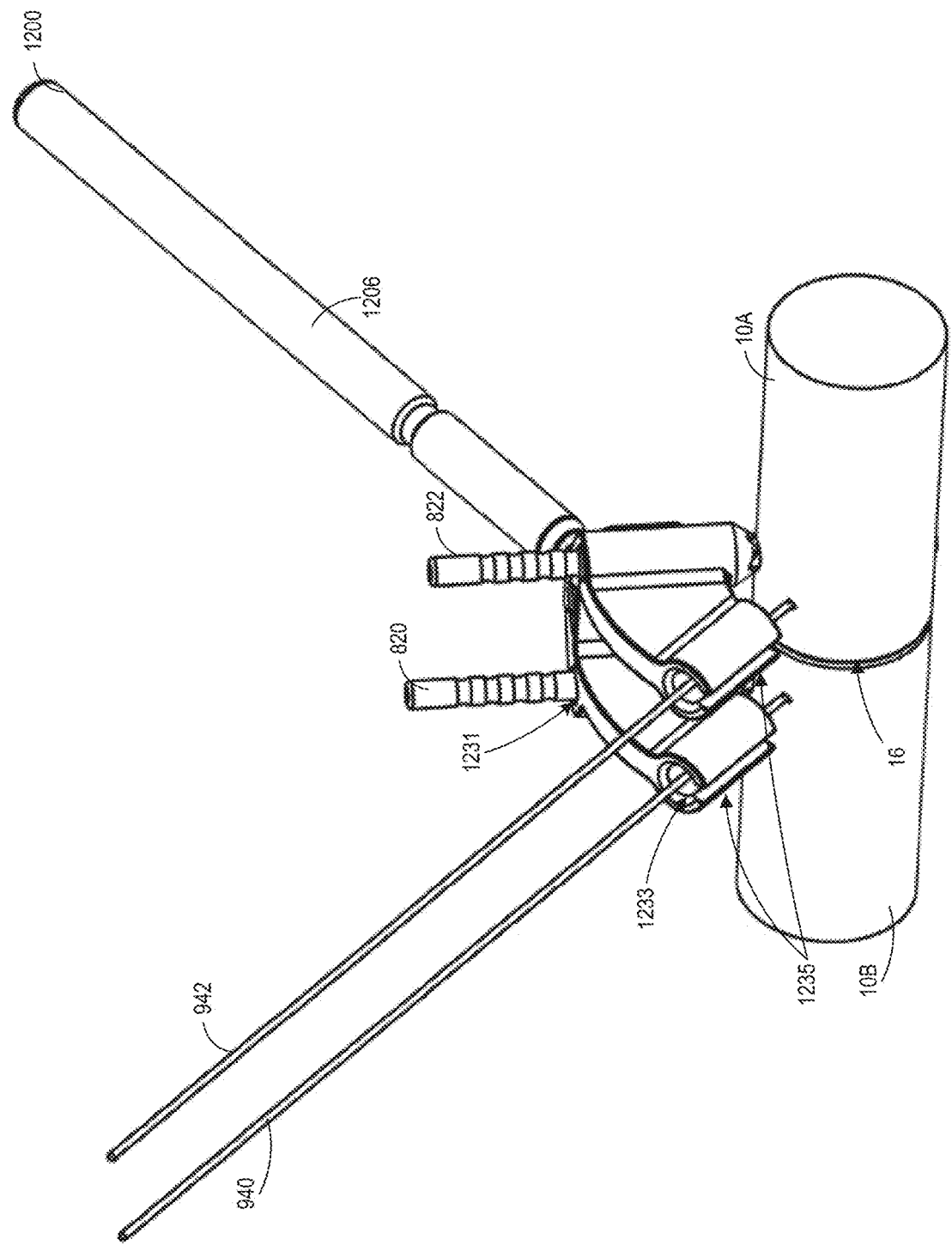

As shown in FIG. 12E, the guide tube 1240 can be removed, leaving the k-wire 940 in the second bone portion 10B. As also shown in FIG. 12E, the guide tube 1240 (or a second guide tube 1240) can be inserted in the other second channel 1233 and the k-wire 942 can be driven into the bone portion 10A via the cannulation 1242 of the second guide tube 1240. The k-wires 940, 942 can be inserted into the second channels 1233 that are on opposite sides of the discontinuity 16 so that the k-wires 940, 942 are parallel. Alternatively, the second channels 1233 may not be symmetrically located about the discontinuity 16 such that the k-wires 940, 942 are at an angle to each other (such as shown in FIG. 9B). As shown in FIG. 12F, the second guide tube 1240 can be removed from the second channel 1233, leaving only the k-wire 942 in the bone portion 10A.

Figure 12G:
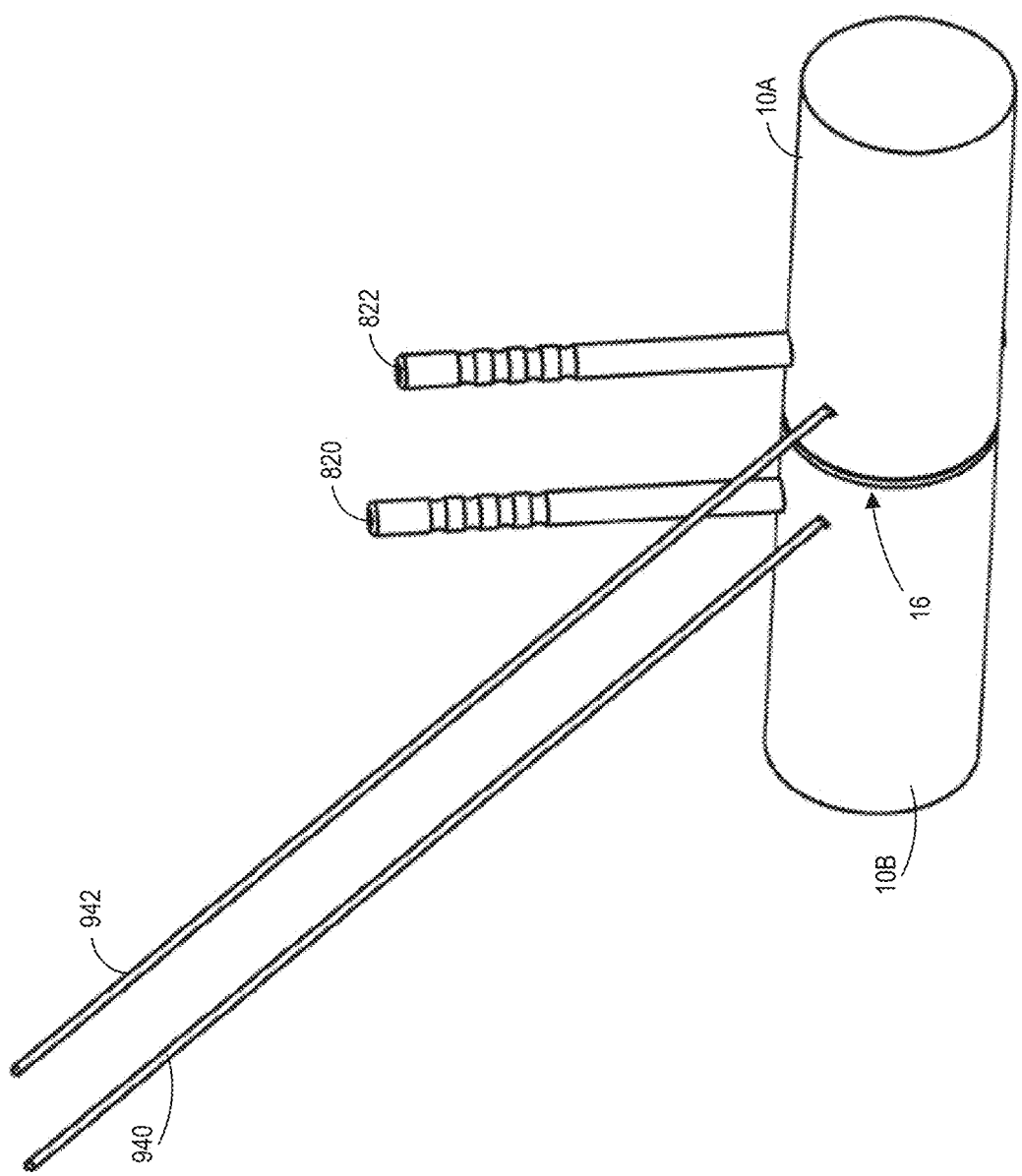

As shown in FIG. 12G, the fourth drill guide 1200 can be disengaged from the temporary fixation pins 822, 824 and the k-wires 940, 942, which are left in the bone portions 10B, 10A respectively. The open slots 1235 of the second channels 1233 allow the fourth drill guide 1200 to clear the k-wires 940, 942 and be removed from the temporary fixation pins 822, 824 by sliding the fourth drill guide 1200 away along the length of the temporary fixation pins 822, 824. In other words, the open slots 1235 allow the fourth drill guide 1200 to be directly removed from the temporary fixation pins 822, 824 despite the k-wires 940, 942 and the temporary fixation pins 822, 824 pointing in different (non-parallel) directions.

Figure 12H:
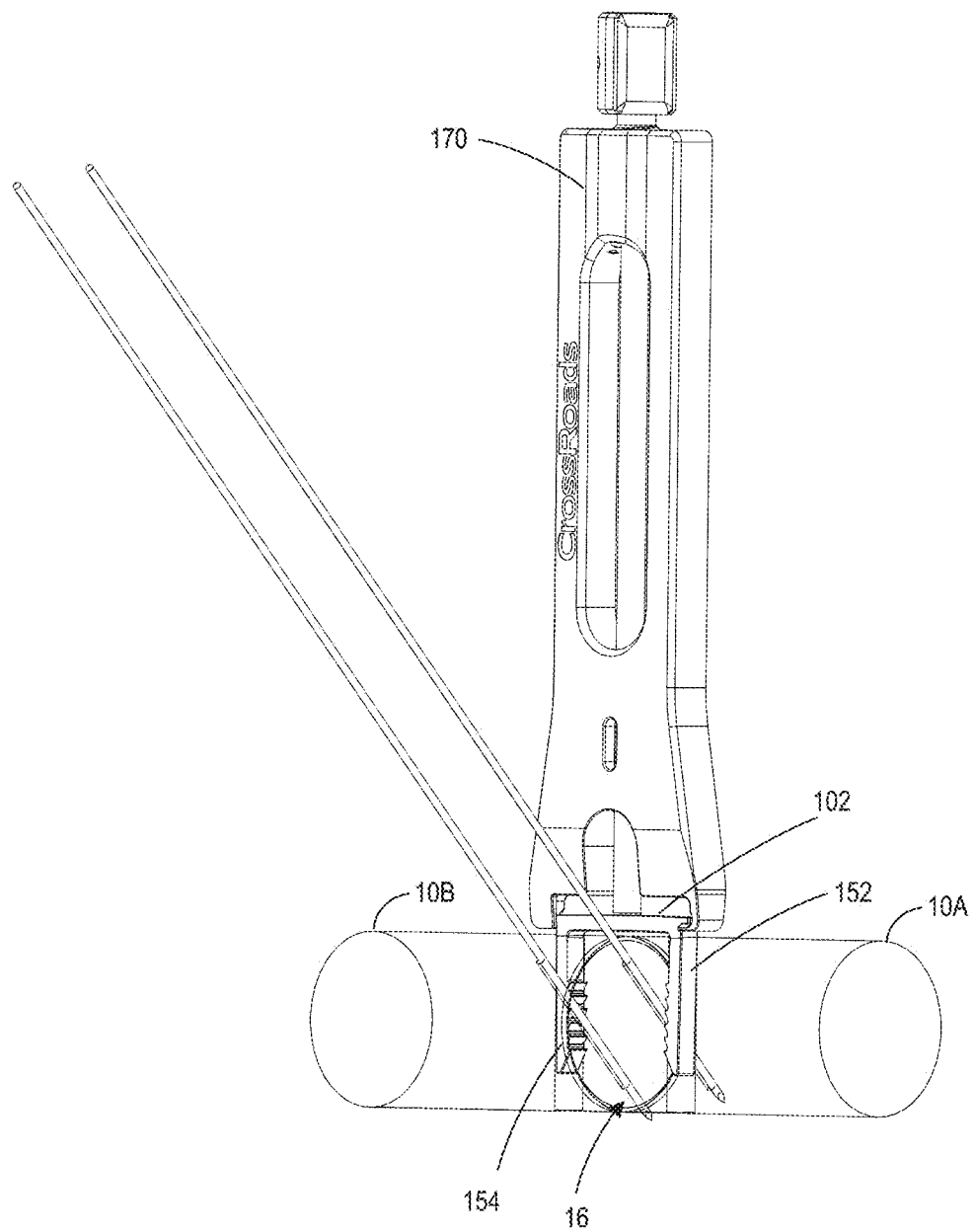
Figure 12I:
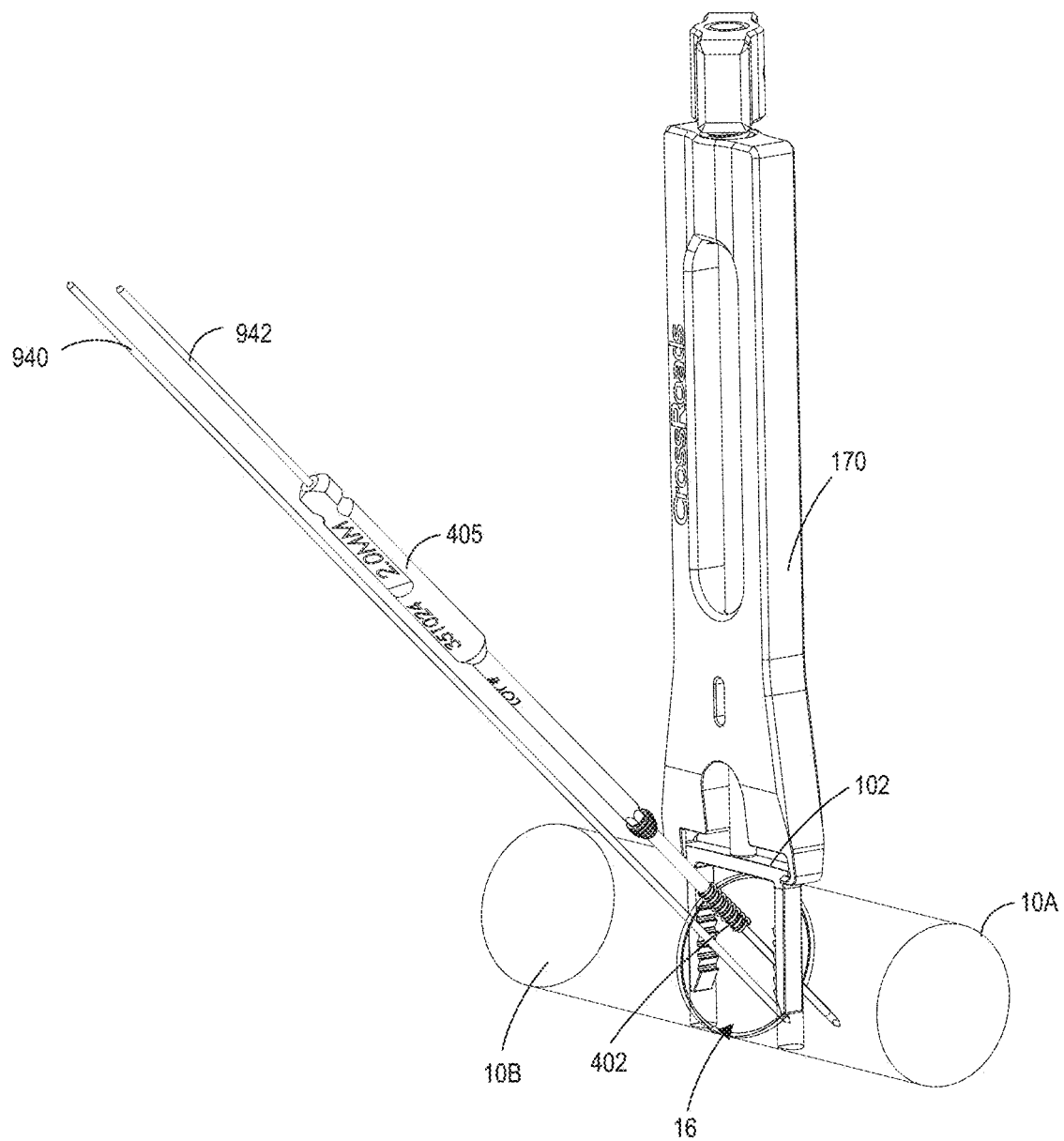
Figure 12J:
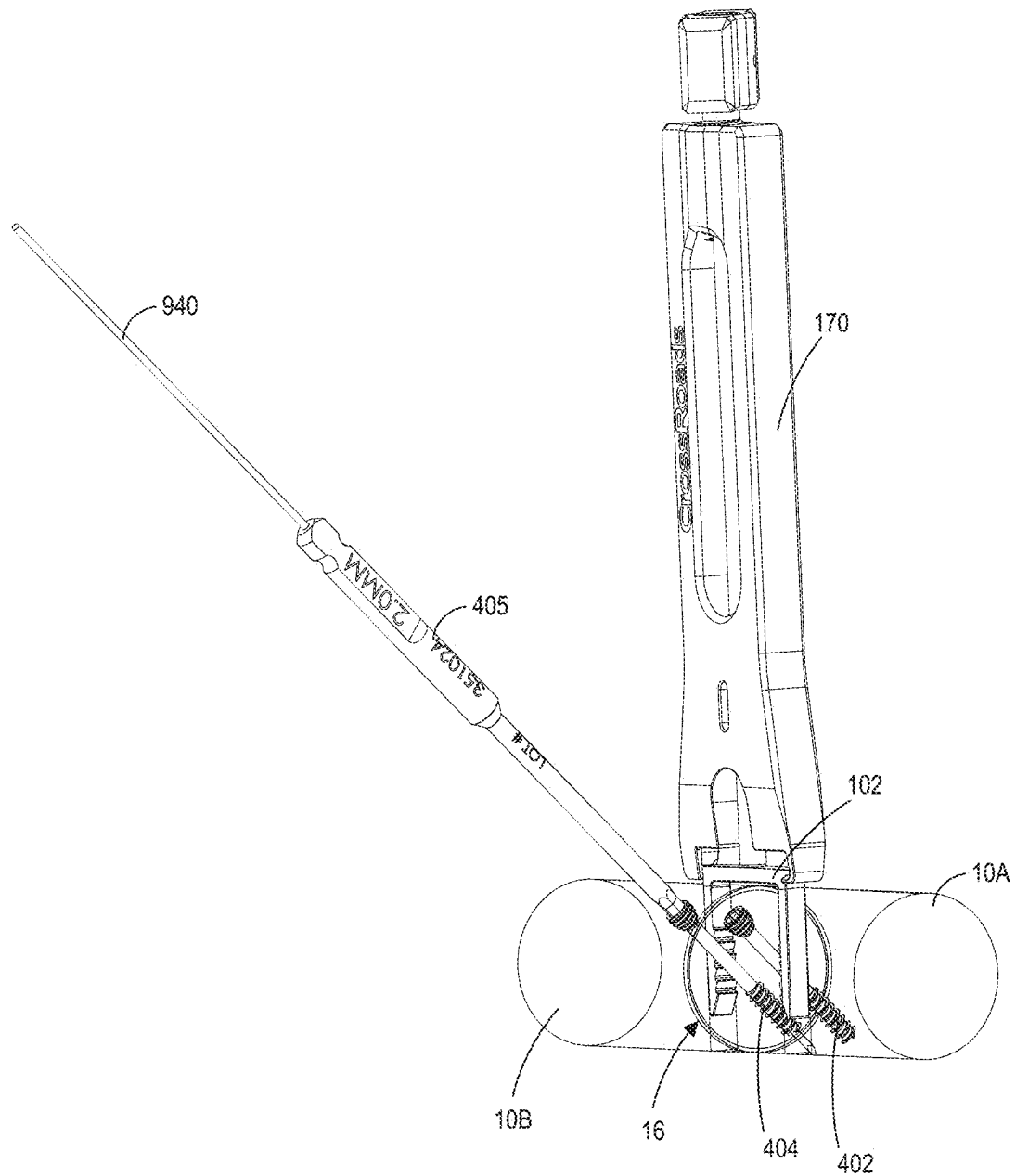

As shown in FIG. 12H, the temporary fixation pins 822, 824 have been removed and the clip 102 in the deformed configuration can be delivered using the inserter tool 170. The legs 152, 154 of the clip 102 can be inserted into the holes previously occupied by the temporary fixation pins 822, 824. The inserter tool 170 can keep the clip 102 in the deformed configuration as described above until the inserter tool 170 is disengaged from the clip 102. With the inserter tool 170 engaged with the clip 102, as shown in FIG. 12I, a cannulated screw 402 can be slid over the k-wires 942 and implanted using a cannulated screwdriver 405. The k-wire 942 can be removed from the bone portion 10A after the screw 402 is implanted. As shown in FIG. 12J, with the inserter tool 170 continuing to be engaged with the clip 102, a cannulated screw 404 can be slid over the k-wires 940 and implanted using the cannulated screwdriver 405. After the screw 404 has been implanted, the k-wire 940 may be removed. A dedicated screwdriver 405 can be used for each screw 402, 404, which may deliver the screws 402, 404. In other embodiments, a single cannulated screwdriver 405 can be used to deliver the screws 402, 404 sequentially in any order.

Figure 12K:
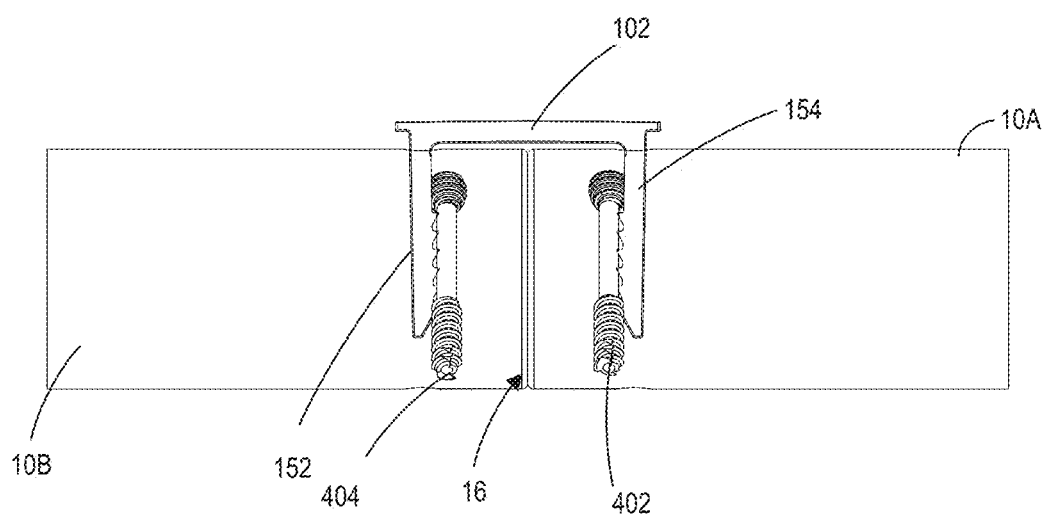

As shown in FIG. 12K, the inserter tool 170 can be removed after the screws 402, 404 have been embedded into the bone portions 10A, 10B. Removing the inserter tool 170 allows the legs 152, 154 to compress towards each other as the clip 102 relaxes towards its free configuration, thereby creating compression across the discontinuity 16. As the legs 152, 154 begin to converge, the legs 152, 154 may contact the screws 402, 404 to distribute the compressive load.

In some instances of fracture fixation, for example, when the quality of the bone is relatively poor due to osteoporosis, trauma, or other reasons, the transfer of force from the clip legs 152, 154 to the bone portions 10A, 10B may be lost due to the soft cancellous bone collapsing under the force from the legs 152, 153. Therefore, by placing a screw 402, 404 in the bone portion 10A, 10B just adjacent to the leg 152, 153, the screw 402, 404 may engage bicortically the higher quality cortical (for example, stronger than the cancellous bone) "shell" of the bone. The fixation force may be transferred from the clip legs 152, 154 to the screw 402, 404, and finally to the higher quality cortical bone. The transfer of fixation forces can preserve the compressive value of the clip legs 152, 154.

Certain Terminology

Terms of orientation used herein, such as "top," "bottom," "proximal," "distal," "longitudinal," "lateral," and "end," are used in the context of the illustrated example. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain examples include or do not include, certain features, elements, and/or steps. Thus, such conditional language is not generally intended to imply that features, elements, and/or steps are in any way required for one or more examples.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

The terms "approximately," "about," and "substantially" as used herein represent an amount close to the stated amount that still performs a desired function or achieves a desired result. For example, in some examples, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

CONCLUSION

Several illustrative examples of implant systems and methodologies have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various examples. All possible combinations and subcombinations of elements and components described herein are intended to be included in this disclosure. No single feature or group of features is necessary or indispensable.

Any portion of any of the steps, processes, structures, and/or devices disclosed or illustrated in one example in this disclosure can be combined or used with (or instead of) any other portion of any of the steps, processes, structures, and/or devices disclosed or illustrated in a different example or flowchart. The examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various examples can be used in all other examples set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the examples described and illustrated in the figures. Many implementation variations are possible based on the disclosure herein. Any of the features, structures, steps, or processes disclosed in this specification can be included in any example.

In summary, various examples of implant systems and related methods have been disclosed. This disclosure extends beyond the specifically disclosed examples to other alternative examples and/or other uses of the examples, as well as to certain modifications and equivalents thereof. Moreover, this disclosure expressly contemplates that various features and aspects of the disclosed examples can be combined with, or substituted for, one another. Accordingly, the scope of this disclosure should not be limited by the particular disclosed examples described above, but should be determined only by a fair reading of the claims.

What is claimed is:

1. A bone fixation system configured to be implanted across a discontinuity in a bone or across a joint between two bones, the system comprising:
   an elongate implant; and
   a clip including a first leg and a second leg, the clip further including a bridge that extends from the first leg to the second leg at first ends of the first and second legs respectively, wherein a distance between second, free ends of the first and second legs opposite the first ends is configured to increase when the clip changes from a first configuration to a second, deformed configuration, wherein, when moving to the second, deformed configuration, the bridge is elastically deformed such that free ends of the first and second legs move away from each other,
   wherein the first leg of the clip is configured to be implanted on a first side of the discontinuity or joint and the second leg of the clip is configured to be implanted on a second side of the discontinuity or joint, and
   wherein the clip is devoid of screw holes that extend through the bridge, such that the elongate implant is configured to be implanted at a location on the first side of the discontinuity or joint, whereby the elongate implant is entirely spaced from the bridge at a location between the first and second legs, and the first leg contacts the elongate implant.

2. The bone fixation system of claim 1, wherein the first and second legs of the clip have a length such that the second, free ends of the first and second legs are configured to terminate in a cancellous portion of the bone or bone portions when implanted.

3. The bone fixation system of claim 1, wherein the elongate implant comprises a screw and the screw has a length that is configured to achieve bicortical purchase when implanted.

4. The bone fixation system of claim 3, wherein screw is a first screw, and the bone fixation system further comprises a second screw that is configured to be implanted at a second location on the second side of the discontinuity or joint, whereby the second screw is entirely spaced from the bridge, and the second leg abuts the second screw.

5. The bone fixation system of claim 4, wherein the bridge and the first and second legs combine to define a plane, and the first and second screws are configured to be implanted along a direction that is angularly offset with respect to the plane.

6. The bone fixation system of claim 5, wherein the first and second screws define respective heads, the first and second screws define respective shafts that extend out with respect to the respective heads, and the respective shafts are threaded along respective entireties of their lengths.

7. The bone fixation system of claim 5, wherein the first and second screws are non-cannulated.

8. The bone fixation system of claim 5, wherein the first and second screws define respective heads and respective shafts that extend out with respect to the respective heads, and the first and second screws are threaded along only portions of their respective shafts.

9. A drill guide configured to deliver the system of claim 1, wherein the elongate implant comprises first and second elongate implants, the drill guide comprising:
a fist pair of locating holes configured to guide a drill bit to drill holes on opposite sides of the discontinuity or joint for receiving the first and second legs of the clip;
at least one second pair of locating holes configured to guide the drill bit or a different drill bit or bone punch to form holes on opposite sides of the discontinuity for receiving the first and second elongate implants, or to guide insertion of k-wires on opposite sides of the discontinuity for receiving the first and second elongate implants.

10. The drill guide of claim 9, wherein the first pair of locating holes and the at least one second pair of locating holes are located on a single component.

11. The drill guide of claim 9, wherein the at least one second pair of locating holes are offset from the first pair of locating holes by a distance and the at least one second pair of locating holes are separated by a shorter distance than the first pair of locating holes.

12. The drill guide of claim 9, wherein the at least one second pair of locating holes are configured to guide the drill bit or the other different drill bit or bone punch to form holes, or to guide insertion of the k-wires without crossing the discontinuity.

13. The drill guide of claim 9, wherein the at least one second pair of locating holes comprise two or more pair of locating holes that are at different angles to the first pair of locating holes.

14. A surgical guide system configured to aid in delivering the system of claim 1, the system comprising:
a clip drill guide configured to be positioned across the discontinuity or joint, the clip drill guide comprising a first cannula configured to be positioned on the first side of the discontinuity or joint and a second cannula configured to be positioned on the second side of the discontinuity or joint; and
an implant guide configured to be positioned on the first or second side of the discontinuity or joint, the implant guide comprising a plurality of implant positioning holes running through the implant guide and a plurality of guide positioning holes running through the implant guide, the plurality of implant positioning holes being separated from the plurality of guide positioning holes by a distance.

15. The surgical guide system of claim 14, comprising a first temporary pin configured to be inserted through the first cannula and into a first clip leg hole in the bone or bone portions drilled through the first cannula, and a second temporary pin configured to be inserted through the second cannula and into a second clip leg hole in the bone or bone portions drilled through the second cannula.

16. The surgical guide system of claim 14, wherein the plurality of implant positioning holes are configured to receive a hole creation device configured to form a first implant hole or a second implant hole in the bone or bone portions, wherein the plurality of implant positioning holes are configured to guide the hole creation device or the k-wire through the bone or bone portions without crossing the discontinuity or joint.

17. The surgical guide system of claim 14, wherein the plurality of implant positioning holes are positioned closer to the discontinuity or joint than the plurality of guide positioning holes.

18. The surgical guide system of claim 14, wherein the implant guide is arc-shaped, the plurality of implant positioning holes passing through the implant guide at varying angles and the plurality of guide positioning holes passing through the implant guide at varying angles.

19. A bone fixation construct comprising:
a bone screw; and
a clip including a first leg, a second leg, and a bridge that extends from a first end of the first leg to a first end of the second leg, wherein the bridge is elastically flexible such second ends of the first and second legs opposite the first ends are biased toward each other,
wherein the bridge and the first and second legs define a plane, the bone screw is oriented at an angle with respect to the plane, and one of the first and second legs is in contact with the bone screw, such that the one of the first and second legs urges the bone screw toward the other of the first and second legs.

20. The bone fixation construct of claim 19, wherein the bone screw is a first bone screw and the one of the first and second legs is defined by the first leg, the bone fixation construct further comprising a second bone screw that is oriented at a respective angle with respect to the plane, and the second leg is in contact with the second bone screw, such that the second leg urges the bone screw implant toward the first leg.

* * * * *